United States Patent [19]

Mohacsi et al.

[11] Patent Number: 4,652,561
[45] Date of Patent: Mar. 24, 1987

[54] NAPHTHO[1,2-B]-1,4-THIAZEPINONES

[75] Inventors: Erno Mohacsi, Summit; Jay P. O'Brien, Cedar Grove, both of N.J.

[73] Assignee: Hoffmann-La Roche Inc., Nutley, N.J.

[21] Appl. No.: 834,178

[22] Filed: Feb. 26, 1986

[51] Int. Cl.$^4$ .................. A61K 31/55; C07D 281/02
[52] U.S. Cl. ...................................... 514/211; 540/488
[58] Field of Search ................. 260/239.3 T; 514/211

[56] References Cited

U.S. PATENT DOCUMENTS

| | | | |
|---|---|---|---|
| 3,562,257 | 2/1971 | Kugita et al. | 260/239.3 B |
| 4,438,035 | 3/1984 | Gaino et al. | 260/239.3 B |
| 4,490,292 | 12/1984 | Maki et al. | 260/239.3 B |
| 4,547,495 | 10/1985 | Maiorana et al. | 260/239.3 B |
| 4,566,995 | 1/1986 | Simonovitch et al. | 260/239.3 B |
| 4,567,175 | 1/1986 | Takeda et al. | 260/239.3 B |

OTHER PUBLICATIONS

Kugita et al, Chem. Pharm. Bull. 18 (10) 2028–2037 (1970).
Kugita et al, Chem. Pharm. Bull. 19 595–602 (1971).
Meshi et al, Chem. Pharm. Bull. 19 (8) 1546–1556 (1971).
Sato et al, Arzneim-Forsch. (Drug. Res.) Jahrgant 21 Nr. 9 (1971) 1338–1342.
Inoue et al, Chem. Soc. Perkin Trans. I (1984) 1725–1732.
CA 71(15): 70657j.
CA 77(1): 5554h.
CA 75(9): 63848b.
CA 75(5): 36165v.
CA 74(25): 141721a.
CA 78(19): 119419u.
CA 75(9): 61652j.
CA 97(18): 150634b.
CA 77(1): 105c
CA 76(11): 59674v.
CA 76(15): 85854y.
CA 78(11): 66993t.
CA 93(21): 197787m.
CA 79(11):66331w.
CA 87(19): 145450c.
CA 97(25): 208153n.
CA 83(7): 58901z.
CA 90(3): 23002z.
CA 90(17): 137874r.
CA 93(23): 215403y.
CA 97(21): 174401z.
CA 96(18): 149164w.
Inoue et al, Chem. Pharm. Bull. 33 (3) 1256–1259 (1985).
CA 73(13): 66641y.
Abstracts of GB 2154-577-A and 578-A.

*Primary Examiner*—Robert T. Bond
*Attorney, Agent, or Firm*—Jon S. Saxe; Bernard S. Leon; Matthew Boxer

[57] ABSTRACT

Compounds of the formula

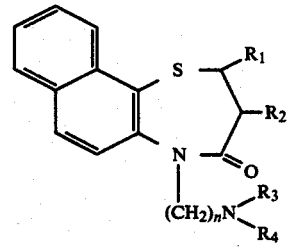

I wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy;

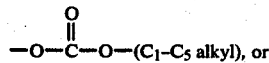

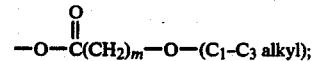

$R_3$ and $R_4$ are independently lower alkyl, phenyl lower alkyl or together form a piperidine or pyrrolidine ring; n is 2 to 4; m is 1 to 2; or pharmaceutically acceptable acid addition salts thereof are described. The compounds of formula I have activity as calcium channel blockers and accordingly, are useful as agents for lowering blood pressure, and as agents for treating ischemia.

43 Claims, No Drawings

NAPHTHO[1,2-B]-1,4-THIAZEPINONES

BRIEF SUMMARY OF THE INVENTION

The invention relates to compounds of the formula

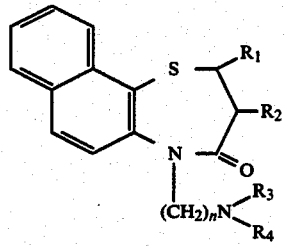

I wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy, $$-O-\overset{O}{\underset{\|}{C}}O-(C_1-C_5 \text{ alkyl}), \text{ or}$$

$$-O-\overset{O}{\underset{\|}{C}}(CH_2)_m-O-(C_1-C_3 \text{ alkyl});$$

$R_3$ and $R_4$ are independently lower alkyl, phenyl lower alkyl or together form a piperidine or pyrrolidine ring; n is 2 to 4; m is 1 to 2; and pharmaceutically acceptable acid additions salts thereof.

The compounds of formula I are active as calcium channel blockers, and accordingly are useful as agents for treating ischemia and as agents for lowering blood pressure.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl, and the like. Alternatively, the number of carbon atoms in an alkyl group is designated herein as in "$C_1-C_3$ alkyl" which denotes a straight or branched chain alkyl group containing 1 to 3 carbon atoms. The term "lower alkoxy" denotes a straight or branched chain lower alkoxy group containing 1 to 4 carbon atoms, for example, methoxy, ethoxy, propoxy, isopropoxy, butoxy, and the like. The term "halogen" denotes the halogens, that is, bromine, chlorine, fluorine and iodine. The term "lower alkanoyloxy" denotes a straight or branched chain alkanoyloxy group of 2 to 5 carbon atoms, for example, acetyloxy, propionyloxy, butyryloxy, isopropionyloxy and the like. The term "lower cycloalkyl" denotes a lower cycloalkyl group containing 3 to 6 carbon atoms, for example, cyclopropyl, cyclobutyl, cyclopentyl, and cyclohexyl. The term "phenyl lower alkyl" denotes a lower alkyl substituted by a phenyl, for example, phenylmethyl, phenylethyl, phenylpropyl, phenylbutyl and the like. The compounds of formula I are active as calcium antagonists, that is, calcium channel blockers, and accordingly, are useful as agents for lowering blood pressure and as agents for the treatment of ischemia.

The invention relates to compounds of the formula

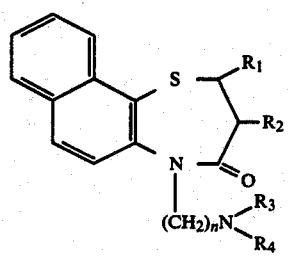

I wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy, $$-O-\overset{O}{\underset{\|}{C}}-O-(C_1-C_5 \text{ alkyl}), \text{ or}$$

$$-O-\overset{O}{\underset{\|}{C}}(CH_2)_m-O-(C_1-C_3 \text{ alkyl});$$

$R_3$ and $R_4$ are independently lower alkyl, phenyl lower alkyl or together form a piperidine or pyrrolidine ring; n is 2 to 4; and m is 1 to 2; and pharmaceutically acceptable acid addition salts thereof.

As used in the formulas herein a solid line (◂) indicates a substituent that is above the plane of the sulfur and nitrogen containing ring, a dotted line ( ) indicates a substituent that is below the plane of the sulfur and nitrogen containing ring.

The compounds of formula I contain 2 asymmetric centers at the 2- and 3-positions. Accordingly, the compounds of formula I can be stereoisomers, that is cis or trans isomers.

As used herein, the term "cis" denotes a compound wherein the $R_1$ and $R_2$ substituents are both on the same side of the plane of the sulfur and nitrogen containing ring. As used herein the term "(+)-cis" denotes an enantiomer having an absolute configuration analogous to that of (2S,3S)-3-(acetyloxy)-2,3-dihydro-2-(4-methoxyphenyl)-5-[2-(dimethylamino)ethyl]naptho[1,2-b]-1,4-thiazepin-4(5H)-one, which is a (+)-cis compound of the invention.

A compound of the formula

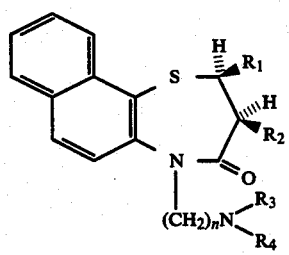

I' wherein $R_1$, $R_2$, $R_3$, $R_4$ and n are as described above is a (+)-cis compound of the invention.

A compound of the formula

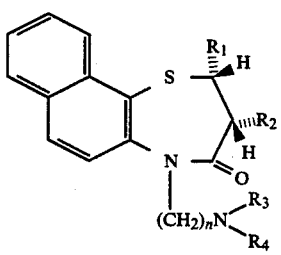

I'' wherein $R_1$, $R_2$, $R_3$, $R_4$ and n are as described above is the enantiomer of a compound of formula I' and a $(-)$-cis compound of the invention.

Preferred compounds of the invention are cis compounds.

Especially preferred compounds of the invention are $(+)$-cis compounds.

As used herein the term "trans" denotes a compound of formula I wherein the $R_1$ and $R_2$ substituents are on opposite sides of the plane of the sulfur and nitrogen containing ring.

A compound of the formula

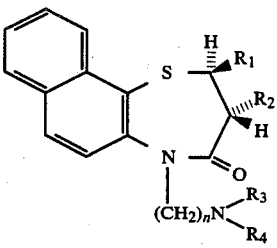

I''' wherein $R_1$, $R_2$, $R_3$, $R_4$, and n are as described above is a trans compound of the invention.

A compound of the formula

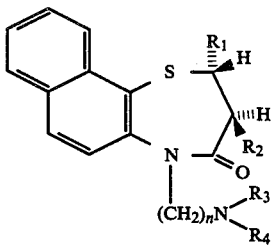

I$^{IV}$ wherein $R_1$, $R_2$, $R_3$, $R_4$, and n are as described above is the enantiomer of a compound of formula I''', and another trans compound of the invention.

Preferred compounds of formula I are those wherein $R_1$ is 4-lower alkoxyphenyl and $R_2$ is lower alkoxy. Of these, as has been pointed out above, cis compounds are preferred and $(+)$-cis compounds are especially preferred.

Other preferred compounds of formula I are those wherein $R_1$ is 4-lower alkoxyphenyl and $R_2$ is

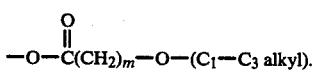

Of these, as has been pointed out above, cis compounds are preferred and $(+)$-cis compounds are especially preferred.

Yet other preferred compounds of formula I are those wherein $R_1$ is 4-lower alkoxyphenyl and $R_2$ is lower cycloalkylcarbonyloxy. Of these, as has been pointed out above, cis compounds are preferred and $(+)$-cis compounds are especially preferred.

Still other preferred compounds of formula I are those wherein $R_1$ is 4-lower alkoxyphenyl and $R_2$ is

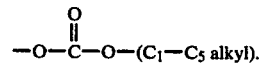

Of these, as has been pointed out above, cis compounds are preferred and $(+)$-cis compounds are especially preferred.

Other preferred compounds of formula I are those wherein $R_1$ is 4-lower alkoxyphenyl, $R_2$ is hydroxy or lower alkanoyloxy $R_3$ is phenyl lower alkyl, $R_4$ is lower alkyl and n is 2 to 3. Of these, as has been pointed out above, cis compounds are preferred and $(+)$-cis compounds are especially preferred.

Preferred compounds of formula I are those wherein $R_1$ is 4-lower alkoxyphenyl; $R_2$ is lower alkanoyloxy; n is 2 to 3; and $R_3$ and $R_4$ are each independently lower alkyl. Of these, as has been pointed out above, cis compounds are preferred and $(+)$-cis compounds are especially preferred.

More preferred compounds of formula I are those wherein $R_1$ is 4-ethoxyphenyl, or more preferably 4-methoxyphenyl; $R_2$ is propionyloxy or more preferably acetyloxy; n is 2; and $R_3$ and $R_4$ are each ethyl or more preferably are each methyl. Of these, as has been pointed above, cis compounds are preferred and $(+)$-cis compounds are especially preferred. Exemplary of compounds of formula I are:

($\pm$)-cis-2,3-Dihydro-3-methoxy-5-[2-(dimethylamino)ethyl]-2-(4-methoxyphenyl)naphtho[1,2-b]-1,4-thiazepin-4(5H)-one;

($\pm$)-cis-2,3-Dihydro-3-[4-(methoxyacetyl)oxy]-2-(4-methoxyphenyl)-5-[2-(dimethylamino)ethyl]naphtho[1,2-b]-1,4-thiazepin-4(5H)-one;

($\pm$)-cis-3-[(Ethoxycarbonyl)oxy]-2,3-dihydro-2-(4-methoxyphenyl)-5-[2-(dimethylamino)ethyl]naphtho[1,2-b]-1,4-thiazepin-4(5H)-one;

($\pm$)-cis-3-[(Cyclopropylcarbonyl)oxy]-2,3-dihydro-5-[2-(dimethylamino)ethyl]-2-(4-methoxyphenyl)naphtho[1,2-b]-1,4-thiazepin-4(5H)-one;

($\pm$)-cis-5-[2-(Diethylamino)ethyl]-2,3-dihydro-3-hydroxy-2-(4-methoxyphenyl)naphtho[1,2-b]-1,4-thiazepin-4(5H)-one;

($\pm$)-cis-3-(Acetyloxy)-5-[2-(diethylamino)ethyl]-2,3-dihydro-2-(4-methoxyphenyl)naphtho[1,2-b]-1,4-thiazepin-4(5H)-one;

($\pm$)-cis-2,3-Dihydro-3-hydroxy-5-[3-(dimethylamino)propyl]-2-(4-methoxyphenyl)naphtho[1,2-b]-1,4-thiazepin-4(5H)-one;

($\pm$)-cis-3-(Acetyloxy)-2,3-dihydro-5-[3-(dimethylamino)propyl]-2-(4-methoxyphenyl)naphtho[1,2-b]-1,4-thiazepin-4(5H)-one;

($-$)-cis-3-(Acetyloxy)-2,3-dihydro-2-(4-methoxyphenyl)-5-[2-(dimethylamino)ethyl]naptho[1,2-b]-1,4-thiazepin-4(5H)-one;

($-$)-cis-2,3-Dihydro-3-hydroxy-2-(4-methoxyphenyl)-5-[2-(dimethylamino)ethyl]naphtho[1,2-b]-1,4-thiazepin-4(5H)-one;

(±)-trans-2,3-Dihydro-3-hydroxy-2-(4-methoxy-phenyl)-5-[2-(dimethylamino)ethyl]naphtho[1,2-b]-1,4-thiazepin-4(5H)-one;

(±)-trans-3-(Acetyloxy)-2,3-dihydro-2-(4-methoxy-phenyl)-5-[2-(dimethylamino)ethyl]naphtho[1,2-b]-1,4-thiazepin-4(5H)-one;

(±)-cis-2,3-Dihydro-3-hydroxy-2-(4-methoxyphenyl)-5-[2-[methyl(phenylmethyl)amino]ethyl]naphtho[1,2-b]-1,4-thiazepin-4(5H)-one; and (±)-cis-3-(Acetyloxy)-2,3-dihydro-2-(4-methoxy-phenyl)-5-[2-[methyl(phenylmethyl)]amino]ethyl]-naphtho[1,2-b]-1,4-thiazepin-4(5H)-one.

Preferred compounds of formula I are:

(±)-cis-5-[2-(Dimethylamino)ethyl]-2,3-dihydro-3-hydroxy-2-(4-methoxyphenyl)naphtho[1,2-b]-1,4-thiazepin-4(5H)-one;

(±)-cis-3-(Acetyloxy)-2,3-dihydro-2-(4-methoxy-phenyl)-5-[2-(dimethylamino)ethyl]naphtho[1,2-b]-1,4-thiazepin-4(5H)-one; and (+)-cis-2,3-Dihydro-3-hydroxy-2-(4-methoxyphenyl)-5-[2-(dimethylamino)ethyl]naphtho[1,2-b]-1,4-thiazepin-4(5H)-one.

A most preferred compound of formula I is:

(+)-cis-3-(Acetyloxy)-2,3-dihydro-2-(4-methoxy-phenyl)-5-[2-(dimethylamino)ethyl]naphtho[1,2-b]-1,4-thiazepin-4(5H)-one.

The preparation of the compounds of formula I is exemplified as hereinafter described.

The compounds of formula I can be prepared as shown in Formula Scheme I below.

Formula Scheme I

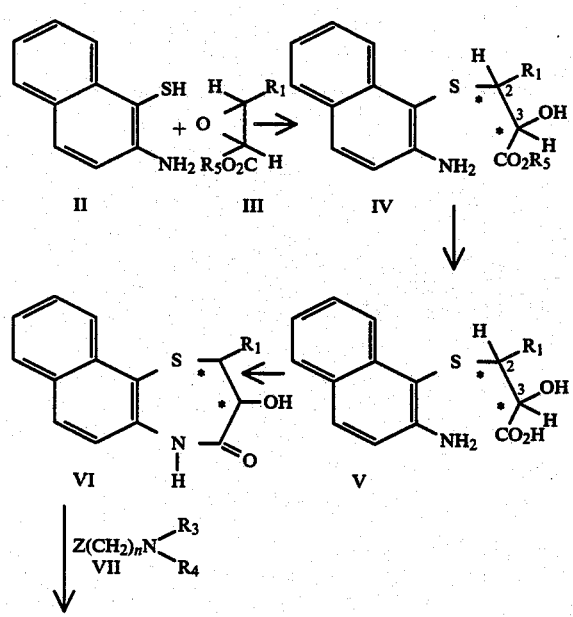

-continued
Formula Scheme I

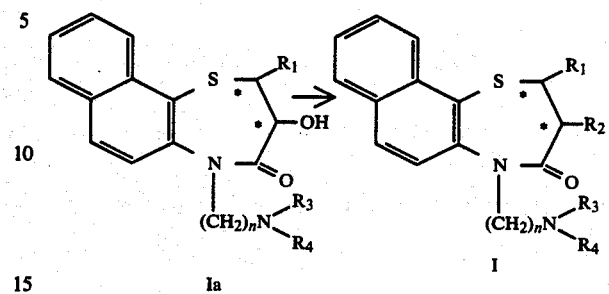

wherein $R_1$, $R_2$, $R_3$, $R_4$ and n are as described above; Z is halogen; $R_5$ is lower alkyl and * is an asymmetric carbon.

In connection with the description below of the reactions in Formula Scheme I, the terms "erythro" and "threo" refer to the relative configurations of the hydroxy and $R_1$ substituents at the 2- and 3-positions of the compounds of formula IV and V. More specifically, the term "erythro" denotes compounds wherein the hydroxy and $R_1$ substituents appear on the same side of the bond between the 2- and 3-positions in a Fischer's Projection Formula. The term "threo" denotes compounds of formula IV and V wherein the hydroxy and $R_1$ substituents appear on the opposite sides of the bond between the 2- and 3-positions in a Fischer's Projection Formula. A Fischer's Projection Formula of an erythro compound of formula V is depicted just below.

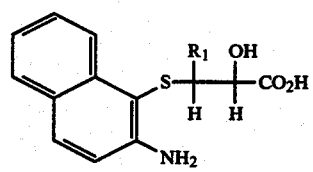

wherein $R_1$ is as described above.

A Fischer's Projection Formula of a threo compound of formula V is depicted just below

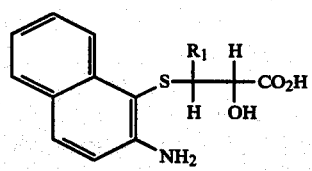

wherein $R_1$ is as described above.

In the reaction description which follows, the erythro compounds of formulas IV and V are obtained in the form of racemates and further reacted in the form of racemates. The threo compounds of formulas IV and V are obtained in the form of racemates and further reacted in the form of racemates.

In connection with Formula Scheme I, 2-aminonaphthylene-1-thiol of formula II is reacted with a compound of the formula

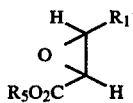

wherein $R_1$ and $R_5$ are as described above, to give a compound of the formula

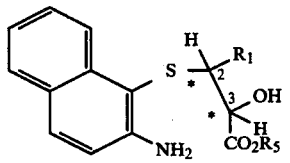

wherein $R_1$, $R_5$, and * are as described above.

The reaction is carried out without solvent or in the presence of an aromatic solvent such as benzene, toluene, xylene, ethylbenzene or acetonitrile in the presence of a catalytic amount of the base potassium carbonate at a temperature in the range of from about 80° to 140° for about 1 to about 20 hours under an argon or more preferably nitrogen atmosphere. The molar ratio of the reactants is not critical. Preferably, the reactants are utilized in the 1:1 molar ratio.

When the reaction is carried out in a non-polar organic solvent preferably toluene, a mixture of erythro and threo compounds of formula IV result. Such a mixture can be separated by treatment with an inorganic anhydrous acid such as anhydrous hydrogen chloride in a polar organic solvent such as ethyl acetate to obtain a hydrochloride salt of an erythro compound. The hydrochloride salt of an erythro compound can be treated with a base such as potassium hydroxide or more preferably sodium hydroxide to obtain an erythro compound.

When the reaction is carried out in acetonitrile in the presence of a catalytic amount of the base potassium carbonate, a threo compound of formula IV results. A threo compound of formula IV can be isolated by chromatography of the reaction mixture followed by recrystallization.

As described above, in the process of the invention, the compound of formula IV can be obtained either as a mixture of erythro and threo compounds or as threo compound depending on the reaction conditions used. The erythro compound of formula IV is used in the next step.

An erythro compound of formula IV can be hydrolyzed to an erythro compound of formula

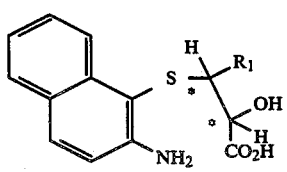

wherein $R_1$ and * are as described above, by conventional hydrolysis methods such as, for example, treatment with an inorganic acid such as, hydrochloric or sulfuric acid, or by treatment with an alkali base such as, potassium hydroxide, or more preferably sodium hydroxide. The reaction is conducted in a polar organic solvent such as, an alkanol like propanol or more preferably ethanol at reflux for a period of about 10 minutes to about 1 hour. Separation of the product, can be by conventional means such as, crystallization.

An erythro compound of formula V can be cyclized to the racemate of the compound of formula

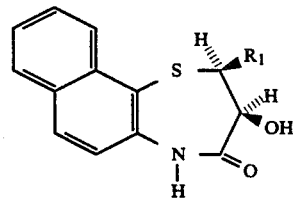

wherein $R_1$ is as described above, by reaction in the presence of a catalytic amount of an acid such as p-toluenesulfonic acid in an aromatic solvent such as, benzene xylene or more preferably toluene, at reflux for a period of about 12 to about 72 hours. Recovery of a compound of formula VI' can be by conventional means such as recrystallization.

The threo racemate of formula IV can be cyclized to the racemate of formula

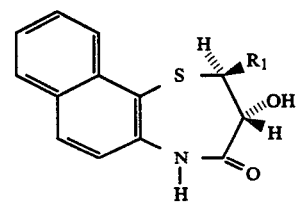

wherein $R_1$ is as described above by heating at reflux in an aqueous inorganic acid such as aqueous sulfuric acid. Recovery of a compound of formula VI" can be by conventional means such as recrystallization.

In the reactions described below, a compound of the formula

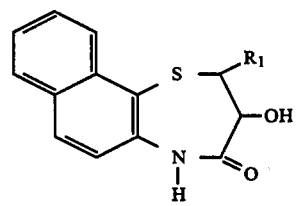

designates either a cis racemate of formula VI' or a trans racemate of formula VI".

Employing a compound of formula VI' in the reactions described below results in a cis compound of formula I of the invention.

Employing a compound of formula VI" in the reactions described below results in a trans compound of formula I of the invention.

A compound of formula VI can be converted to a compound of formula

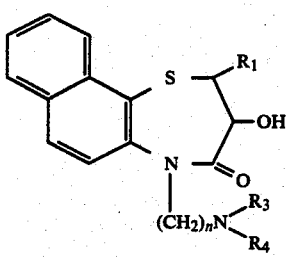

wherein $R_1$, $R_3$, $R_4$ and n are as described above, by reaction with a compound of the formula

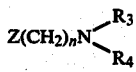

wherein $R_3$, $R_4$ and n are as described above, and Z is halogen, preferably chlorine. The reaction is carried out by reacting an alkali metal salt of a compound of formula VI, such as the sodium or more preferably potassium salt thereof with an aminoalkyl halide of formula VII, preferably the chloride thereof, in a polar organic solvent such as, methyl acetate, or more preferably ethyl acetate, at about 40° to about 80°, or at the reflux temperature of the solvent employed, which in the case of ethyl acetate is 77°, for a period of about 1 hour to about 17 hours. The reaction is carried out in the presence of a base, such as, potassium hydroxide in acetone or more preferably potassium carbonate in acetone or in a lower alkyl acetate. Separation of the compound of formula Ia can be by conventional means such as crystallization.

A compound of formula Ia, which is encompassed by compounds of formula I, can be acylated by reaction with a lower alkanoic anhydride, such as propionic anhydride, acetic anhydride, or a lower alkanoyl halide for example, acetyl, propionyl or butyryl bromide optionally in the presence of a base such as, pyridine, triethylamine, or dimethylaniline at room temperature or up to about 115°.

Alternatively, compounds of formula I wherein $R_2$ is lower alkoxy can be obtained by reacting an alkali metal salt of a compound of formula Ia such as a sodium salt (prepared by reacting a compound of formula Ia with an alkali metal hydride like sodium hydride), with an alkylating agent such as dialkyl sulfate, more particularly dimethyl sulfate in an aromatic solvent such as toluene or more preferably benzene, at about reflux temperature for a period of about 10 minutes to about 2 hours. The resulting compound of formula I can be isolated by conventional means such as crystallization.

Alternatively, a compound of formula I wherein $R_2$ is

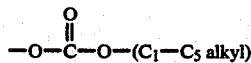

can be obtained by a reaction of a compound of formula Ia with an alkyl halo formate such as ethyl chloroformate in a basic solvent such as pyridine at about ice bath temperatures. The resulting compound of formula I can be isolated by conventional means such as crystallization.

A compound of formula I wherein $R_2$ is

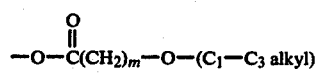

can be prepared by reacting a compound of formula Ia with an alkoxy alkanoyl halide such as, methoxyacetyl chloride in a basic solvent such as pyridine at about ice bath temperatures. The resulting compound of formula I can be isolated by conventional means such as crystallization.

A compound of formula I wherein $R_2$ is cycloalkyl carbonyloxy can be obtained by reacting a compound of formula Ia with a cycloalkylcarboxylic acid halide such as, cyclopropane carboxylic acid chloride in a basic solvent such as pyridine at about ice bath temperatures for about 1 to about 17 hours. The resulting compound of formula I can be isolated by conventional means such as extraction.

A compound of formula I wherein $R_2$ is other than hydroxy can be converted into a corresponding acid addition salt by treatment with an organic acid such as, acetic acid, oxalic acid, malonic acid, tartaric acid, malic acid, citric acid, lactic acid, maleic acid, or fumaric acid and a suitable organic solvent such as, ethyl acetate, acetone, methanol, or ethanol. Alternatively, a compound of formula I wherein $R_2$ is other than hydroxy can be converted into a corresponding acid addition salt by treatment with an inorganic acid such as sulfuric acid, hydrobromic acid, or more preferably hydrochloric acid, except in those instances where the $R_2$ substituent would be cleaved by such treatment. The resulting compound of formula I where $R_2$ is hydroxy can be converted into the corresponding acid addition salt by treatment with an organic acid as described above or an inorganic acid such as, hydrochloric acid, in a suitable organic solvent such as ethyl acetate.

Alternatively, prior to the above described conversion of a compound formula Ia to the other compounds of formula I, and the salt forming steps, a compound of formula Ia which is produced as a racemate can be resolved into its optically active enantiomers. The resolution of a particular compound of formula Ia, that is, (±)-cis-2,3-dihydro-3-hydroxy-2-(4-methoxyphenyl)-5-[2-(dimethylamino)ethyl]naphtho[1,2-b]-1,4-thiazepin-4(5H)-one, is shown in Formula Scheme II. The resolution of other compounds of formula Ia may require, for example, other conventional resolving agents.

Formula Scheme II

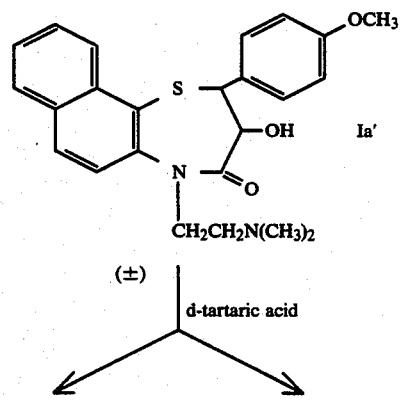

-continued
Formula Scheme II

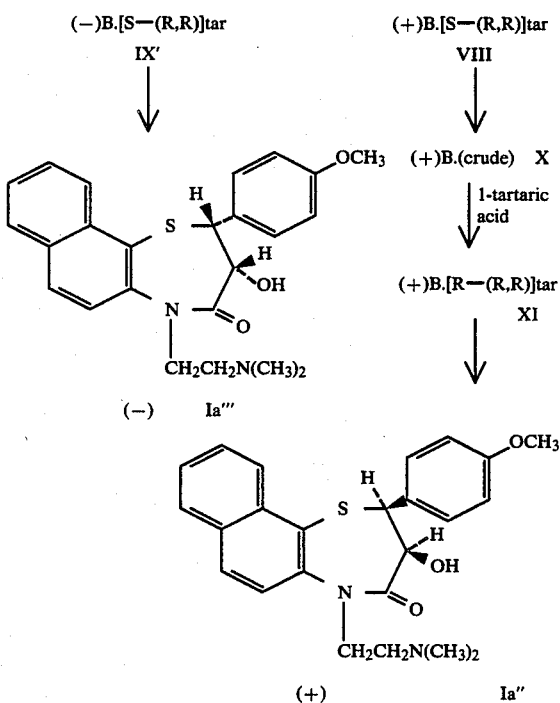

wherein [S-(R,R)]tar is d-tartaric acid; [R-(R,R)]tar is l-tartaric acid; and (+)B and (−)B are respectively the (+)- and (−)-enantiomers of the compound of formula Ia′, (±)-cis-2,3-dihydro-3-hydroxy-2-(4-methoxyphenyl)-5-[2-(dimethylamino)ethyl]naphtho[1,2-b]-1,4-thiazepin-4(5H)-one.

In connection with Formula Scheme II above, a racemate of the formula Ia′ in a lower alkanol, such as, methanol, is treated with a hot methanolic solution of a resolving agent such as d-tartaric acid which is also called S-(R,R)-2,3-dihydroxybutanedioic acid, and the resulting solution is allowed to crystallize at about room temperature. The crystals are a salt of formula IX′ of the resolving agent and the (−)-enantiomer of the compound of formula Ia′. The soluble salt is that of the (+)-enantiomer of the compound of formula Ia′ and the resolving agent. This is the solution of formula VIII in Formula Scheme II above.

The above solution of formula VIII is concentrated and treated in water with a base such as sodium hydroxide or more preferably concentrated ammonium hydroxide and extracted with an organic solvent such as methylene chloride and concentrated to give the crude (+)-enantiomer of formula X of the Formula Scheme II. The crude (+)-enantiomer of formula X can be further purified by dissolving in a hot solution of a lower alkanol such as methanol, and treating the resulting solution with a resolving agent such as l-tartaric acid which is also called R-(R,R)-2,3-dihydroxybutanedioic acid in methanol. A salt of this resolving agent and the (+)-enantiomer of formula XI results. The just above mentioned salt can be suspended in water and treated with a base such as, concentrated ammonium hydroxide, and the resulting suspension can be extracted with organic solvents such as, methylene chloride. The (+)-enantiomer of formula Ia″ can be isolated from the solution by evaporation of the solvent and can be used in the above described reactions for compounds of formula Ia.

The salt of formula IX′ can be treated in water with a base such as sodium hydroxide or more preferably concentrated ammonium hydroxide than the aqueous suspension extracted with an organic solvent such as methylene chloride and concentrated to obtain the (−)-enantiomer of formula Ia‴. This (−)-enantiomer can be used in the above described reactions of compounds of formula Ia.

The compounds of formula II, that is, 2-aminonaphthalene-1-thiol, can be prepared as follows. To a solution of a base such as potassium hydroxide or more preferably sodium hydroxide and an alkylene glycol such as ethylene glycol, is added 2-aminobenzo[g]benzothiazole, which is a known compound or can be prepared according known methods. The mixture is heated at reflux under an inert atmosphere such as nitrogen for about 10 to about 25 hours, diluted with water then neutralized with acetic acid. The aqueous suspension is extracted with ether and the solvent is removed. The compound of formula II, that is, 2-aminonaphthalene-1-thiol, is obtained from the residue by conventional means.

The compounds of formula III, are known compounds or can be prepared according to known methods. Exemplary of compounds of formula III are:
trans-3-(p-methoxyphenyl)glycidate; and
trans-3-(p-ethoxyphenyl)glycidate.

The compounds of formula VII are known compounds or can be prepared according to known methods. Exemplary of the compounds of formula VII are:
2-dimethylaminoethyl chloride;
2-dimethylaminoethyl bromide;
2-diethylaminoethyl chloride;
2-dipropylaminoethyl chloride; and
3-dimethylaminopropyl chloride.

The compounds of formula I, including the pharmaceutically acceptable acid addition salts thereof, are calcium antagonists, more specifically, calcium channel blockers, and are therefore useful as agents in lowering blood pressure and in treating ischemia. In addition, the compounds of formula I in certain instances show calmodulin antagonist activity in the below described ATPase test, which activity is also beneficial. Their pharmocologically useful activities are demonstrated in warm-blooded animals using standard procedures which are set forth below.

BLOOD PRESSURE LOWERING IN THE SPONTANEOUSLY HYPERTENSIVE (SH) RAT

Six male SH rats were used for each test. Body weights were recorded. Six pre-drug control recordings of the systolic blood pressure (mmHg) were measured from the tails of the rats which were unanesthetized and restrained in holders. The rats were previously heated for 5–10 minutes at 32°–34° C. The systolic blood pressure was measured by an occlusion cuff.

The compounds were administered orally to the rats in a composition that included 5% compound and the remainder gum acacia. The blood pressure of the rats was measured over a period of hours following oral administration.

The measure of a compound's ability to decrease blood pressure, is a measure of its ability as an antihypertensive agent.

The activities of compounds of the invention in this test are given in Table I which follows.

GUINEA PIG ILEUM ASSAY—TONIC CONTRACTION

Male guinea-pigs weighing from 300–400 grams were stunned and bled. The abdomen was opened and 10–15 cm of terminal ileum was carefully removed and cleaned and placed in Tyrode's Solution of the following composition: NaCl (8 g/l), KCl (0.2 g/l), MgCl$_2$ (0.2 g/l.). CaCl$_2$ (0.2 g/l). NaH$_2$PO$_4$ (0.05 g/l), NaHCO$_3$ (1.0 g/l) and Glucose (1 g/l). The solution was maintained at 37° C. and gassed with 95%O$_2$ and 5%CO$_2$. Portions of the ileum were placed over a glass rod, a shallow incision was made the length of the mesenteric attachment just severing the outer-longitudinal muscle layer. The longitudinal muscle was separated from the underlying circular muscle by gentle dissection (Rang, H. P. Annals of N.Y. Academy of Science Vol. 144, page 756, (1964)). The tissue was fixed at one end to a tissue holder, the other end was connected by a thread to a force transducer and suspended in a muscle bath containing Tyrode's Solution maintained at 37° C. and gassed with 95%O$_2$ and 5%CO$_2$. An initial tension of 500 mg was applied and the tissue allowed to equilibrate for 60 minutes prior to the start of the study. During this period the tissue was washed every 16 minutes. Each preparation, at 16 minute intervals, was challenged with KCl sufficient to yield a bath K$^+$ concentration of 80 mMK for 2 minutes, then washed with fresh solution. The 16 minute interval between K$^+$ challenges was maintained throughout the study. Upon stabilization of the responses to the K$^+$ challenge the test compound (potential calcium entry antagonist) was introduced into the bath 2 minutes prior to and during the 2 minute exposure to K$^+$ after which the bath was cleared and washed with fresh solution. Logarithmically increasing doses (up to 10$^{-4}$M) of the potential antagonist were administered as the study progressed.

The measure of compound's ability to inhibit the tonic contraction of muscle is a measure of its activity as a calcium channel blocking agent. The IC$_{50}$ is that concentration at which a compound inhibits the tonic contraction of muscle by 50%.

The activity of compounds of the invention in this test is given in the Table II which follows.

Calmodulin (CaM) antagonist activity (ATPase Test)

Calmodulin (CaM) antagonist activity was determined from the inhibition of CaM-activated Ca$^{2+}$-Mg$^{2+}$-ATPase activity in the following test.

Preparation of CaM-deficient erythrocyte membranes

Erythrocyte membranes were prepared from rat according to Luthra et al., Biochim. Biophys. Acta. 418:180, 1976. Packed erythrocytes were washed three times with 0.172M Tris-HCl, pH 7.6. The buffy coat was carefully removed. Erythrocytes hemolysis was induced by addition of 280 ml of distilled water to 20 ml of a 50% suspension of erythrocytes in 0.172M Tris-HCl, pH 7.6. After centrifugation at 27,000×g for 30 minutes, erythrocytes membranes were obtained as a pellet. The pellet was washed 3 times with 20 mM Tris-HCl buffer, pH 7.6 containing 1 mM ethylene glycol bis($\beta$-aminoethyl ether)N,N,N',N'-tetraacetic acid (EGTA) and for the next wash EGTA was omitted. Thus obtained almost white ghosts, that is the erythrocyte membranes, were washed once with 18 mM-18 mM histidine-imidazole buffer, pH 7.1, the resulting pellet of CaM-deficient erythrocyte membranes was suspended in the same buffer to give a final protein concentration of about 2 mg/ml.

Ca$^{2+}$-Mg$^{2+}$-AtPase assay

The ATPase assay used here was essentially the same as that described by Gapinath and Vincenzi, Biochim. Biophys. Res. Commun. 77:1203, 1977. The reaction mixture in a final incubation volume of 1.0 ml contained 2 mM ATP, 18 mM-18 mM histidine-imidazole buffer, pH 7.1, 0.1 mM EGTA, 3 mM MgCl$_2$, 80 mM NaCl, 15 mM KCl, 0.1 mM ouabain, CaM, 200 $\mu$g of erythrocyte ghost proteins and the compound to be tested. CaCl$_2$ (0.2 mM) was present in all tubes except in those for the determination of Mg$^{2+}$-ATPase. The reaction was started by addition of ATP and carried out at 37° C. for 30 min. Inorganic phosphate liberated was determined. Protein was determined using the method of Lowry et al. J. Biol. Chem. 193:265, 1951.

CaM-deficient erythrocyte membranes yield a Ca$^{2+}$-Mg$^{2+}$-ATPase that is stimulated by CaM above the basal activity. The specific activity of the basal Ca$^{2+}$-Mg$^{2+}$-ATPase is about 10 nmoles of inorganic phosphate/mg protein/min and of the maximally activated enzyme 40–50 nmoles of inorganic phosphate/mg protein/min. The CaM concentration was set at 2 units (CaM units are as described by the Sigma Chemical Company) in the following tests. The activity of a test compound was calculated as the percent inhibition of the CaM-stimulated activity. Concentration-response curves were constructed from the percent inhibition versus the concentration of the test compound, and the IC$_{50}$, which is determined graphically, is that concentration of the test compound causing 50% inhibition.

The activity of compounds of this invention in this test is given in Table II which follows.

TABLE I

| | Systolic Blood Pressure (SBP) in the SH rat | |
|---|---|---|
| Compound | SBP ($\Delta$ mm Hg) | Duration (hours) |
| A | −67 ± 7 | 19 |
| B | −63 ± 9 | 24 |

In the above table, the dose is 50 mg/kg p.o.
In the above table, the compounds are as follows:
A is (+)-cis-3-(acetyloxy)-2,3-dihydro-2-(4-methoxyphenyl)-5-[2-(dimethylamino)ethyl]naphtho[1,2-b]-1,4-thiazepin-4(5H)-one;
B is (+)-cis-5-[2-(dimethylamino)ethyl]-2,3-dihydro-3-hydroxy-2-(4-methoxyphenyl)naphtho[1,2-b]-1,4-thiazepin-4(5H)-one.

TABLE II

| Compound | (Guinea Pig Ileum Assay-Tonic Contraction) IC$_{50}$ (M) | (ATPase Test) IC$_{50}$ ($\mu$M) |
|---|---|---|
| A | 1.3 × 10$^{-6}$ | 5.4 |
| B | 1.1 × 10$^{-6}$ | >80 |
| C | 5.2 × 10$^{-7}$ | 17.2 |
| D | 2.3 × 10$^{-7}$ | 6.5 |
| E | 5.6 × 10$^{-5}$ | 17.8 |
| F | — | 9.9 |
| G | 6.3 × 10$^{-5}$ | >80 |
| H | 4.6 × 10$^{-5}$ | 52 |

In the above table, compounds A and B are as previously set forth and the other compounds are as follows:

C is (±)-cis-5-[2-(dimethylamino)ethyl]-2,3-dihydro-3-hydroxy-2-(4-methoxyphenyl)naphtho[1,2-b]-1,4-thiazepin-4(5H)-one;

D is (±)-cis-3-(acetyloxy)-2,3-dihydro-2-(4-methoxyphenyl)-5-[2-(dimethylamino)ethyl]naphtho[1,2-b]-1,4-thiazepin-4(5H)-one;

E is (−)-cis-2,3-dihydro-3-hydroxy-2-(4-methoxyphenyl)-5-[2-(dimethylamino)ethyl]naphtho[1,2-b]-1,4-thiazepin-4(5H)-one;

F is (−)-cis-3-(acetyloxy)-2,3-dihydro-2-(4-methoxyphenyl)-5-[2-(dimethoxylamino)ethyl]naphtho[1,2-b]-1,4-thiazepin-4(5H)-one;

G is (±)-trans-2,3-dihydro-3-hydroxy-2-(4-methoxyphenyl)-5-[2-(dimethylamino)ethyl]naphtho[1,2-b]-1,4-thiazepin-4(5H)-one;

H is (±)-trans-3-(acetyloxy)-2,3-dihydro-2-(4-methoxyphenyl)-5-[2-(dimethylamino)ethyl]naphtho[1,2-b]-1,4-thiazepin-4(5H)-one.

The compounds of formula I, and the pharmaceutically acceptable acid addition salts thereof, as herein described, can be incorporated into standard pharmaceutical dosage forms. The compounds of formula I are useful for oral or parenteral application with the usual pharmaceutical carrier materials, for example, organic or inorganic inert carrier materials, such as water, gelatin, lactose, starch, magnesium stearate, talc, vegetable oils, gums, polyalkylene glycols, and the like. The pharmaceutical preparations can be employed in a solid form, for example, as tablets, or capsules, or in liquid form, for example as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The invention also relates to a method of inducing calcium antagonist activity in a warm-blooded animal in need of such treatment which comprises administering an effective amount of a compound of formula I. The invention also relates to a method of lowering blood pressure or treating ischemia by bringing about myocardial preservation during ischemia, which comprises administering an effective amount of a compound of formula I, or pharmaceutically acceptable acid addition salts thereof to a warm-blooded animal in need of such treatment. The amount of an oral daily dosage can be determined by one skilled in the art and would be comparable to that of diltiazem. The amount of an intravenous dosage can also be determined by one skilled in the art and is comparable to that of diltiazem. It is to be understood, however, that dosages may vary from individual to individual and accordingly the above recitation is not intended to limit the scope of the present invention in any way.

The following examples further illustrate the invention. All temperatures are in degrees C., unless otherwise mentioned.

EXAMPLE 1

2-Aminobenzo[g]benzothiazole

To 160 mL of thionyl chloride 64.0 g of N-(2-naphthyl)-β-thiourea was added portionwise while the temperature of the reaction mixture was kept at 30°–40° (internal temperature). After the addition was completed, an additional 80 mL of thionyl chloride was added and the mixture was heated at 50°–55° for 4 hours. It was cooled to room temperature and diluted with 400 mL of ethyl acetate and filtered. The filtrate in 400 mL of water was basified with concentrated ammonium hydroxide. The aqueous suspension was shaken with 300 mL ethyl acetate, then the product was separated by filtration and dried to give 54.1 g (85%) of 2-aminobenzo[g]benzothiazole, mp 258°–260°.

EXAMPLE 2

2-Aminonaphthalene-1-thiol

To a solution of 30.0 g sodium hydroxide in 30 mL of water and 140 mL of ethylene glycol was added 18.0 g of 2-aminobenzo[g]benzothiazole. The mixture was heated at reflux under nitrogen for 20 hours and diluted with 80 mL of water. After cooling, the mixture was filtered, then the filtrate was chilled in an ice-bath and neutralized with acetic acid. The aqueous suspension was extracted with ether (3×200 mL) and the combined extracts were dried (magnesium sulfate). Removal of the solvent gave the product to which heptane (3×150 mL) was added and the solvent was removed under reduced pressure. (This step removed traces of acetic acid). The yield of the 2-aminonaphthalene-1-thiol was 15.4 g (97%), mp 108°–110°. A sample of this compound was recrystallized from ethanol, mp 109°–110°. This compound is sensitive to air and therefore was used immediately in the next step of the synthetic scheme.

EXAMPLE 3

(±)erythro- and threo-[(2-Amino-1-naphthalenyl)thio]-2-hydroxy-3-(4-methoxyphenyl)propanoic Acid Methyl Ester Under nitrogen, a mixture of 15.0 g of 2-aminonaphthalene-1-thiol and 17.8 g of trans-3-(p-methoxyphenyl)glycidate in 150 mL of toluene was stirred and heated at reflux over a period of 17 hours. The solvent was removed under reduced pressure to give 35.0 g (97%) of a mixture of (±)-erythro- and threo-[(2-amino-1-naphthalenyl)thio]-2-hydroxy-3-(4-methoxyphenyl)propanoic acid methyl ester. (The erythro/threo ratio of this oil was 8:1, as determined by NMR spectrometry.) The mixture of title compounds, on treatment with hydrogen chloride (anhydrous) in ethyl acetate afforded 31.7 g (88%) of (±)-erythro-[(2-amino-1-naphthalenyl)thio]-2-hydroxy-3-(4-methoxyphenyl)propanoic acid methyl ester hydrochloride, mp 172°–174°. A sample was recrystallized from methanol—ether, mp 183°–185° (d).

Calcd: C, 60.07; H, 5.28; N, 3.34. Found: C, 59.87; H, 5.35; N, 3.33.

The hydrochloride salt (8.3 g) on treatment with dilute sodium hydroxide and extraction of the aqueous suspension with ethyl acetate gave after removal of the solvent 7.5 g (99%) of (±)-erythro-[(2-amino-1-naphthalenyl)thio]-2-(hydroxy-3-(4-methoxyphenyl)-propanoic acid methyl ester. A sample of this compound was crystallized from ether, mp 109°–110°.

EXAMPLE 4

(±)-erythro-[(2-Amino-1-naphthalenyl)thio]-2-hydroxy-3-(4-methoxyphenyl)propanoic Acid Methyl Ester Under nitrogen, a mixture of 14.1 g of 2-aminonaphthalene-1-thiol and 16.6 g of trans-3-(p-methoxyphenyl)glycidate was stirred and heated first at 140° for one hour, then at 165° for six hours. After cooling, the mixture was dissolved in acetonitrile—ethyl acetate and on treatment with hydrogen chloride (anhydrous) afforded 22.6 g (67%) of (±)-erythro-[(2-amino-1-naphthalenyl)thio]-2-hydroxy-3-(4-methoxyphenyl)-propanoic acid methyl ester hydrochloride, mp 170°–172°.

EXAMPLE 4a (±)-threo-[(2-Amino-1-naphthalenyl)thio]-2-hydroxy-3-(4-methoxyphenyl)propanoic Acid Methyl Ester Under nitrogen, a mixture of 5.3 g of 2-aminonaphthalene-1-thiol, 6.2 g of trans-3-(p-methoxyphenyl)-glycidate and 0.6 g of potassium carbonate in 80 mL of acetonitrile was stirred at reflux for 2 hours. After cooling to room temperature, the mixture was filtered and the filtrate was concentrated to a volume of about 20 mL. The crystals were separated by filtration to give 1.4 g of 2H-naphtho[1,2-b]-1,4-thiazin-3(4H)-one, mp 211°–212°. The mother liquors after removal of 1.4 g of the above compound were concentrated under reduced pressure to give 11.0 g of a mixture of (±)-threo-[(2-amino-1-naphthalenyl)thio]-2-hydroxy-3-(4-methoxyphenyl)propanoic acid methyl ester, 2H-naphtho[1,2-b]-1,4-thiazin-3(4H)-one and p-methoxybenzaldehyde. The mixture was chromatographed on a column using 120 g of silica gel. The column was eluted with 75 mL portions of methylene chloride. The first six portions of which were collected and the solvent was removed under reduced pressure gave 1.1 g of an oil, whose nuclear magnetic resonance spectrum was identical with that of p-methoxybenzaldehyde. Further elution of the column with the same solvent (fractions 7–19) afforded 1.0 g of 2H-naphtho[1,2-b]-1,4-thiazin-3(4H)-one. A sample of this compound was recrystallized from ethanol, mp 211°–212°. (±)-threo-[(2-Amino-1-naphthalenyl)thio]-2-hydroxy-3-(4-methoxyphenyl)propanoic acid methyl ester was obtained from the column by further elution with methylene chloride. The methylene chloride fractions 20–35 were combined and the solvent was removed under reduced pressure to afford 1.2 g of (±)-threo-[(2-amino-1-naphthalenyl)thio]-2-hydroxy-3-(4-methoxyphenyl)propanoic acid methyl ester, which was treated with hydrogen chloride (anhydrous) in ethyl acetate to afford 1.1 g (85%) of the hydrochloride of (±)-threo-[(2-amino-1-naphthalenyl)thio]-2-hydroxy-3-(4-methoxyphenyl)-propanoic acid methyl ester, mp 139°–140°. The hydrochloride salt (1.1 g) on treatment with dilute sodium hydroxide and extraction of the aqueous suspension with ethyl acetate gave after removal of the solvent 1.0 g of (±)-threo-[(2-amino-1-naphthalenyl)thio]-2-hydroxy-3-(4-methoxyphenyl)propanoic acid methyl ester. A sample of this compound was recrystallized from ether—pet. ether, mp. 32°–34°.

Calcd: C, 65.78; H, 5.52; N, 3.65. Found: C, 65.71; H, 5.54; N, 3.57.

EXAMPLE 5

(±)-erythro-[(2-Amino-1-naphthalenyl)thio]-2-hydroxy-3-(4-methoxyphenyl)propanoic Acid A mixture of 22.0 g of (±)-erythro-[(2-amino-1-naphthalenyl)thio]-2-hydroxy-3-(4-methoxyphenyl)-propanoic acid methyl ester and 36 mL 1N sodium hydroxide in 150 mL of ethanol was heated at reflux for 30 minutes. After removal of about 100 mL of ethanol the mixture was diluted with water (60 mL) and extracted with ether (100 mL). The aqueous solution was chilled, acidified with acetic acid and extracted with ethyl acetate (3×100 mL). The combined ethyl acetate solutions were washed with brine and dried (magnesium sulfate). Removal of the solvent at reduced pressure gave 19.0 g of (±)-erythro-[(2-amino-1-naphthalenyl)thio]-2-hydroxy-3-(4-methoxyphenyl)-propanoic acid which after recrystallization from acetonitrile afforded 17.1 g (81%) of pure (±)-erythro-[(2-amino-1-naphthalenyl)thio]-2-hydroxy-3-(4-methoxyphenyl)propanoic acid, mp 171°–173°.

Calcd: C, 65.03; H, 5.19; N, 3.79. Found: C, 64.83; H, 5.35; N, 3.76.

EXAMPLE 6

(±)-cis-2,3-Dihydro-3-hydroxy-2-(4-methoxyphenyl)-naphtho[1,2-b]-1,4-thiazepin-4(5H)-one A mixture of 2.0 g of (±)-erythro-[(2-amino-1-naphthalenyl)thio]-2-hydroxy-3-(4-methoxyphenyl)-propanoic acid and a few crystals of p-toluenesulfonic acid in 150 mL of toluene was heated at reflux for 72 hrs. Removal of the solvent gave 1.7 g (89%) of (±)-cis-2,3-dihydro-3-hydroxy-2-(4-methoxyphenyl)naphtho[1,2-b]-1,4-thiazepin-4(5H)-one, mp 208°–210°. A sample was recrystallized from ethyl acetate, mp 209°–210°.

Calcd: C, 68.37; H, 4.88; N, 3.99. Found: C, 68.36; H, 4.96; N, 4.40.

EXAMPLE 7

(±)-trans-2,3-Dihydro-3-hydroxy-2-(4-methoxyphenyl)naphtho[1,2-b]-1,4-thiazepin-4(5H)-one A mixture of 2.0 g of (±)-threo-[(2-amino-1-naphthalenyl)thio]-2-hydroxy-3-(4-methoxyphenyl)-propanoic acid methyl ester and 200 mL of 20% aqueous sulfuric acid was stirred and heated at reflux for 1.5 hours. After cooling, the crystals were separated by filtration and recrystallization from acetonitrile afforded 0.9 g (47%) of (±)-trans-2,3-dihydro-3-hydroxy-2-(4-methoxyphenyl)naphtho[1,2-b]-1,4-thiazepin-4(5H)-one, mp 232°–234°.

Calcd: C, 68.37; H, 4.88; N, 3.99. Found: C, 68.09; H, 4.86; N, 4.06.

EXAMPLE 8

(±)-cis-5-[2-(Dimethylamino)ethyl]-2,3-dihydro-3-hydroxy-2-(4-methoxyphenyl)naphtho[1,2-b]-1,4-thiazepin-4(5H)-one A mixture of 1.4 g of (±)-cis-2,3-dihydro-3-hydroxy-2-(4-methoxyphenyl)naphtho[1,2-b]-1,4-thiazepin-4(5H)-one, 0.6 g of powdered potassium carbonate and 0.5 g of 2-dimethylaminoethyl chloride in 30 mL of ethyl acetate was stirred and heated at reflux for 3 hours, then twice an additional 0.150 g of 2-dimethylaminoethyl chloride was added at 2 hour intervals. The mixture was heated at reflux for a total of 12 hours then was cooled to room temperature and filtered. The filrate was diluted with ethyl acetate, washed with brine (40 mL) and dried (magnesium sulfate). Removal of the solvent gave 1.7 g of product, which after crystallization from ethyl acetate—ether afforded 1.3 g (81%) of (±)-cis-5-[2-(dimethylamino)ethyl]-2,3-dihydro-3-hydroxy-2-(4-methoxyphenyl)naphtho[1,2-b]-1,4-thiazepin-4(5H)-one, mp 148°–149°.

Calcd: C, 68.23; H, 6.20; N, 6.63. Found: C, 68.03; H, 6.11; N, 6.54.

The above base (1.3 g) on treatment with hydrogen chloride (anhydrous) in ethyl acetate gave the hydrochloride which after recrystallization from acetone— ethyl acetate afforded 1.3 g (83%) of (±)-cis-5-[2-(dimethylamino)ethyl]2,3-dihydro-3-hydroxy-2-(4-methoxyphenyl)naphtho[1,2-b]-1,4-thiazepin-4(5H)-one hydrochloride, mp 267°–268°.

Calcd: C, 62.80; H, 5.71; N, 6.10. Found: C, 62.76; H, 5.88; N, 6.04.

EXAMPLE 9

(±)-cis-3-(Acetyloxy)-2,3-dihydro-2-(4-methoxyphenyl)-5-[2-(dimethylamino)ethyl]naphtho[1,2-b]-1,4-thiazepin-4(5H)-one A mixture of 1.1 g of (±)-cis-5-[2-(dimethylamino)ethyl]-2,3-dihydro-3-hydroxy-2-(4-methoxyphenyl)-naphtho[1,2-b]-1,4-thiazepin-4(5H)-one hydrochloride and 20 mL of acetic anhydride was heated at 100° for 17 hours. The excess reagent was removed under reduced pressure and the residue was partitioned between dilute sodium hydroxide and ethyl acetate. The ethyl acetate solution was washed with brine, then dried (magnesium sulfate) and removal of the solvent gave 1.1 g (99%) of (±)-cis-3-(acetyloxy)-2,3-dihydro-2-(4-methoxyphenyl)-5-[2-(dimethylamino)ethyl]-naphtho[1,2-b]-1,4-thiazepin-4(5H)-one. A sample was crystallized from ether, mp 122°–124°.

Calcd: C, 67.22; H, 6.08; N, 6.03. Found: C, 67.30; H, 6.19; N, 6.04.

The above base (1.1 g) on treatment with hydrogen chloride (anhydrous) in ethyl acetate afforded 1.0 g of (±)-cis-3-(acetyloxy)-2,3-dihydro-2-(4-methoxyphenyl)-5-[2-(dimethylamino)ethyl]naphtho[1,2-b]-1,4-thiazepin-4(5H)-one hydrochloride. A sample was recrystallized from ethanol—ethyl acetate, mp 238°–239°.

Calcd: C, 62.33; H, 5.83; N, 5.59. Found: C, 62.14; H, 5.84; N, 5.56.

EXAMPLE 10

(±)-trans-2,3-dihydro-3-hydroxy-2-(4-methoxyphenyl)-5-[2-(dimethylamino)ethyl]naphtho[1,2-b]-1,4-thiazepin-4(5H)-one A mixture of 2.2 g of (±)-trans-2,3-dihydro-3-hydroxy-2-(4-methoxyphenyl)naphtho[1,2-b]-1,4-thiazepin-4(5H)-one, 1.0 g of powdered potassium carbonate and 0.8 g of 2-dimethylaminoethyl chloride in 50 mL of ethyl acetate was stirred and heated at reflux for 2 hours, then an additional 0.2 g of 2-dimethylaminoethyl chloride was added three times at 2 hour intervals. The mixture was heated at reflux for a total of 12 hours and the solvent was removed under reduced pressure. The residue was partitioned between water and methylene chloride. The methylene chloride solution was washed with water and dried (magnesium sulfate). Removal of the solvent at reduced pressure gave 2.5 g of product which after crystallization from ethyl acetate afforded 2.0 g (76%) of (±)-trans-2,3-dihydro-3-hydroxy-2-(4-methoxyphenyl)-5-[2-(dimethylamino)ethyl]naphtho[1,2-b]-1,4-thiazepin-4(5H)-one, mp 160°–161°.

Calcd: C, 68.23; H, 6.20; N, 6.63. Found: C, 68.01; H, 6.41; N, 6.76.

The above base (2.0 g) on treatment with hydrogen chloride (anhydrous) in ethyl acetate afforded 2.0 g (92%) of (±)-trans-2,3-dihydro-3-hydroxy-2-(4-methoxyphenyl)-5-[2-(dimethylamino)ethyl]naphtho[1,2-b]-1,4-thiazepin-4(5H)-one hydrochloride, mp 194°–195°. A sample was recrystallized from acetone, mp 194°–195°.

Calcd: C, 62.80; H, 5.71; N, 6.10. Found: C, 62.69; H, 5.59; N, 6.28.

EXAMPLE 11

(±)-trans-3-(Acetyloxy)-2,3-dihydro-2-(4-methoxyphenyl)-5-[2-(dimethylamino)ethyl]naphtho[1,2-b]-1,4-thiazepin-4(5H)-one A mixture of 1.1 g of (±)-trans-5-[2-(dimethylamino)ethyl]-2,3-dihydro-3-hydroxy-2-(4-methoxyphenyl)naphtho[1,2-b]-1,4-thiazepin-4(5H)-one hydrochloride and 20 mL acetic anhydride was heated at 100° for 17 hours. The excess reagent was removed under reduced pressure and the residue was partitioned between ethyl acetate and dilute sodium hydroxide. The ethyl acetate solution was washed with brine and dried (magnesium sulfate). Removal of the solvent gave 1.0 g (91%) of (±)-trans-3-(acetyloxy)-2,3-dihydro-2-(4-methoxyphenyl)-5-[2-(dimethylamino)ethyl]naphtho[1,2-b]-1,4-thiazepin-4(5H)-one. A sample was crystallized from ether—pet. ether, mp 122°–123°.

Calcd: C, 67.22; H, 6.08; N, 6.03. Found: C, 67.07; H, 6.21; N, 5.98.

The above base (1.0 g) on treatment with hydrogen chloride (anhydrous) in ethyl acetate afforded 0.7 g (65%) of (±)-trans-3-(acetyloxy)-2,3-dihydro-2-(4-methoxyphenyl)-5-[2-(dimethylamino)ethyl]naphtho[1,2-b]-1,4-thiazepin-4(5H)-one hydrochloride, mp 156°–157°.

Calcd: C, 62.33; H, 5.83; N, 5.59. Found: C, 62.19; H, 6.06; N, 5.60.

EXAMPLE 12

(±)-cis-2,3-Dihydro-3-hydroxy-2-(4-methoxyphenyl)-5-[2-(dimethylamino)ethyl]naphtho[1,2-b]-1,4-thiazepin-4(5H)-one [S-(R,R)]-2,3-dihydroxybutanedioate A hot solution of 11.9 g of (±)-cis-2,3-dihydro-3-hydroxy-2-(4-methoxyphenyl)-5-[2-(dimethylamino)ethyl]naphtho[1,2-b]-1,4-thiazepin-4(5H)-one in 600 mL of methanol was combined with a hot solution of 4.23 g of d-tartaric acid in 200 mL of methanol. The clear solution was allowed to crystallize at room temperature for 17 hours. The crystals were separated by filtration and dried to yield 8.5 g of product, mp 195°–197° (d). One recrystallization from methanol (650 mL) yielded 5.9 g (72%) of (−)-cis-2,3-dihydro-3-hydroxy-2-(4-methoxyphenyl)-5-[2-(dimethylamino)ethyl]naphtho[1,2-b]-1,4-thiazepin-4(5H)-one [S-(R,R)]2,3-dihydroxybutanedioate semihydrate, mp 202°–204° (d), $[\alpha]_D^{25} -16.92°$ (C 0.56, MeOH).

Calcd: C, 57.81; H, 5.72; N, 4.81. Found: C, 57.64; H, 5.50; N, 4.85.

EXAMPLE 13

(−)-cis-2,3-Dihydro-3-hydroxy-2-(4-methoxyphenyl)-5-[2-(dimethylamino)ethyl]naphtho[1,2-b]-1,4-thiazepin-4(5H)one (−)-cis-2,3-Dihydro-3-hydroxy-2-(4-methoxyphenyl)-5-[2-(dimethylamino)ethyl]naphtho[1,2-b]-1,4-thiazepin-4(5H)-one [S-(R,R)]-2,3-dihydroxybutanedioate semihydrate, 5.9 g in 50 mL of water was decomposed with concentrated ammonium hydroxide. The resulting suspension was extracted with methylene chloride (3×100 mL). The combined methylene chloride solutions were washed with water (50 mL) and dried (magnesium sulfate). Removal of the solvent gave 4.2 g (98%) of (−)-cis-2,3-dihydro-3-hydroxy-2-(4- methoxyphenyl)-5-[2-(dimethylamino)ethyl]naph-tho[1,2-b]-1,4-thiazepin-4(5H)-one. A sample was recrystallized from ethyl acetate, mp 170°–171°, $[\alpha]_D^{25}$ −42.09° (C 0.64, MeOH). A 100 MH$_2$ NMR spectrum of the title compound in chloroform in the presence of chiral shift reagent Eu(TFC)$_3$ indicated that the sample was enantiomerically pure.

Calcd: C, 68.23; H, 6.20; N, 6.63. Found: C, 68.09; H, 6.21; N, 6.64.

The above base (4.5 g) on treatment with hydrogen chloride (anhydrous) in ethyl acetate gave the hydrochloride, which after recrystallization from methanol—ethanol afforded 4.3 g (90%) of (−)-cis-2,3-dihydro-3-hydroxy-2-(4-methoxyphenyl)-5-[2-(dimethylamino)ethyl]naphtho[1,2-b]-1,4-thiazepin-4(5H)-one hydrochloride, mp 259°–261°, $[\alpha]_D^{25}$ −20.45° (C 0.518, MeOH).

Calcd: C, 62.80; H, 5.71; N, 6.10. Found: C, 62.68; H, 5.91; N, 6.20.

EXAMPLE 14

(+)-cis-2,3-Dihydro-3-hydroxy-2-(4-methoxyphenyl)-5-[2-(dimethylamino)ethyl]naphtho[1,2-b]-1,4-thiazepin-4(5H)-one [R-(R,R)]-2,3-Dihydroxybutanedioate The combined mother liquors obtained in Example 12 above were concentrated to dryness. The residue in 50 mL of water was decomposed with concentrated ammonium hydroxide, and the resulting suspension was extracted with methylene chloride (3×100 mL). The combined extracts were washed with water (50 mL) and dried (magnesium sulfate). Removal of the solvent gave 7.6 g of crude (+)-cis-2,3-dihydro-3-hydroxy-2-(4-methoxyphenyl)-5-[2-(dimethylamino)ethyl]naphtho[1,2-b]-1,4-thiazepin-4(5H)-one. The base (7.6 g) was dissolved in 380 mL of hot methanol and combined with a hot solution of 2.7 g of 1-tartaric acid in 100 mL of methanol. The solution was allowed to crystallized at room temperature for 6 hours. The crystals were collected by filtration and dried to yield 7.5 g of product, mp 201°–203° (d). One recrystallization from 700 mL methanol yielded 6.7 g (82%) of (+)-cis-2,3-dihydro-3-hydroxy-2-(4-methoxyphenyl)-5-[(2-(dimethylamino)ethyl]naphtho[1,2-b]-1,4-thiazepin-4(5H)-one [R-(R,R)]-2,3-dihydroxybutanedioate semihydrate, mp 202°–204° (d), $[\alpha]_D^{25}$ +19.43° (C 0.45, MeOH).

Calcd: C, 57.81; H, 5.72; N, 4.81. Found: C, 57.69; H, 5.86; N, 4.88.

EXAMPLE 15

(+)-cis-2,3-Dihydro-3-hydroxy-2-(4-methoxyphenyl)-5-[2-(dimethylamino)ethyl]naphtho[1,2-b]-1,4-thiazepin-4(5H)-one (+)-cis-2,3-Dihydro-3-hydroxy-2-(4-methoxyphenyl)-5-[2-(dimethylamino)ethyl]naphtho[1,2-b]-1,4-thiazepin-4(5H)-one [R-(R,R)]-2,3-dihydroxybutanedioate semihydrate, 6.7 g in 50 mL of water was decomposed with concentrated ammonium hydroxide. The resulting suspension was extracted with methylene chloride (3×100 mL). The combined methylene chloride solutions were washed with water (50 mL) and dried (magnesium sulfate). Removal of the solvent gave 4.8 g (98%) of (+)-cis-2,3-dihydro-3-hydroxy-2-(4-methoxyphenyl)-5-[2-(dimethylamino)ethyl]naphtho[1,2-b]-1,4-thiazepin-4(5H)-one. A sample was recrystallized from ethyl acetate, mp 170°–172°, $[\alpha]_D^{25}$ +39.98° (C 0.48, MeOH).

Calcd: C, 68.23; H, 6.20; N, 6.63. Found: C, 68.04; H, 6.20; N, 6.74.

The above base (5.0 g) on treatment with hydrogen chloride (anhydrous) in ethyl acetate gave product which after recrystallization from methanol-ethanol afforded 4.2 g (78%) of (+)-cis-2,3-dihydro-3-hydroxy-2-(4-methoxyphenyl)-5-[2-(dimethylamino)ethyl]naphtho[1,2-b]-1,4-thiazepin-4(5H)-one hydrochloride, mp 260°–262°, $[\alpha]_D^{25}$ +18.52° (C 0.54, MeOH).

Calcd: C, 62.80; H, 5.93; N, 6.10. Found: C, 62.60; H, 6.16; N, 6.11.

EXAMPLE 16

(−)-cis-3-(Acetyloxy)-2,3-dihydro-2-(4-methoxyphenyl)-5-[2-(dimethylamino)ethyl]naphtho[1,2-b]-1,4-thiazepin-4(5H)-one A mixture of 3.0 g (−)-cis-2,3-dihydro-3-hydroxy-2-(4-methoxyphenyl)-5-[2-(dimethylamino)ethyl]naphtho[1,2-b]-1,4-thiazepin-4(5H)-one hydrochloride and 5 mL of acetic anhydride was stirred at 100° for 17 hours. The excess reagent was removed under reduced pressure and to the residue, ice-water was added. The resulting suspension was made basic with concentrated ammonium hydroxide and extracted with methylene chloride. The combined extracts were washed with water (10 mL) and dried (magnesium sulfate). Removal of the solvent under reduced pressure gave 2.5 g (83%) of (−)-cis-3-(acetyloxy)-2,3-dihydro-2-(4-methoxyphenyl)-5-[2-(dimethylamino)ethyl]naphtho[1,2-b]-1,4-thiazepin-4(5H)-one as an amorphous substance, $[\alpha]_D^{25}$ −10.1° (C 0.57, MeOH).

Calcd: C, 67.22; H, 6.08; N, 6.03. Found: C, 66.87; H, 6.20; N, 6.00.

The above base (2.5 g) on treatment with hydrogen chloride (anhydrous) in ethyl acetate gave the hydrochloride, which after recrystallization from acetone—ether afforded 2.4 g of (−)-cis-3-(acetyloxy)-2,3-dihydro-2-(4-methoxyphenyl)-5-[2-(dimethylamino)ethyl]naphtho[1,2-b]-1,4-thiazepin-4(5H)-one hydrochloride, mp 228°–230°, $[\alpha]_D^{25}$ −2.42° (C 0.57, MeOH).

Calcd: C, 62.33; H, 5.83; N, 5.59. Found: C, 62.20; H, 6.05; N, 5.57.

EXAMPLE 17

(+)-cis-3-(Acetyloxy)-2,3-dihydro-2-(4-methoxyphenyl)-5-[2-(dimethylamino)ethyl]naphtho[1,2-b]-1,4-thiazepin-4(5H)-one A mixture of 3.6 g of (+)-cis-2,3-dihydro-3-hydroxy-2-(4-methoxyphenyl)-5-[2-(dimethylamino)ethyl]naphtho[1,2-b]-1,4-thiazepin-4(5H)-one hydrochloride and 6 mL acetic anhydride was stirred at 100° for 7 hours. The excess reagent was removed under reduced pressure and to the residue ice-water was added. The resulting suspension was made basic with concentrated ammonium hydroxide and extracted with methylene chloride. The combined methylene chloride solutions were washed with water (15 mL) and dried (magnesium sulfate). Removal of the solvent at reduced pressure gave 3.6 g (98%) of (+)-cis-3-(acetyloxy)-2,3-dihydro-2-(4-methoxyphenyl)-5-[2-(dimethylamino)ethyl]naphtho[1,2-b]-1,4-thiazepin-4(5H)-one as an amorphous compound, $[\alpha]_D^{25}$ +11.02° (C 0.56, MeOH).

Calcd: C, 67.22; H, 6.02; N, 6.03. Found: C, 66.96; H, 6.20; N, 5.96.

The above base (3.6 g) on treatment with hydrogen chloride (anhydrous) in ethyl acetate gave the hydrochloride, which after recrystallization from acetone—ether afforded 3.3 g (87%) of (+)-cis-3-(acetyloxy)-2,3-dihydro-2-(4-methoxyphenyl)-5-[2-(dimethylamino)ethyl]naphtho[1,2-b]-1,4-thiazepin-4(5H)-one hydrochloride, mp 229°–231°, $[\alpha]_D^{25}+4.72°$ (C 0.52, MeOH).

Calcd: C, 62.33; H, 5.83; N, 5.59. Found: C, 62.25; H, 5.92; N, 5.50.

EXAMPLE 18

(±)-cis-3-[(Ethoxycarbonyl)oxy]-2,3-dihydro-2-(4-methoxyphenyl)-5-[2-(dimethylamino)ethyl]naphtho[1,2-b]-1,4-thiazepin-4(5H)-one To a solution of 0.8 g of (±)-cis-2,3-dihydro-3-hydroxy-2-(4-methoxyphenyl)-5-[2-(dimethylamino)ethyl]naphtho[1,2-b]-1,4-thiazepin-4(5H)-one in 10 mL of pyridine (dried over potassiuwm hydroxide) in an ice-bath, 0.4 g of ethyl chloroformate was added dropwise then stored in the freezer overnight. The mixture was concentrated under reduced pressure and the residue was partitioned between ether and dilute sodium hydroxide. The ether solution was washed with brine then dried (magnesium sulfate) and removal of the solvent gave 0.9 g (97%) of (±)-cis-3-[(ethoxycarbonyl)oxy]-2,3-dihydro-2-(4-methoxyphenyl)-5-[2-(dimethylamino)ethyl]naphtho[1,2-b]-1,4-thiazepin-4(5H)-one. A sample was crystallized from ether—pet. ether, mp 168°–169°.

Calcd: C, 65.57; H, 6.11; N, 5.67. Found: C, 65.41; H, 6.31; N, 5.53.

The above base (0.9 g) on treatment with hydrogen chloride (anhydrous) in acetone afforded 0.93 g (96%) of (±)-cis-3-[(ethoxycarbonyl)oxy]-2,3-dihydro-2-(4-methoxyphenyl)-5-[2-(dimethylamino)ethyl]naphtho[1,2-b]-1,4-thiazepin-4(5H)-one hydrochloride, mp 138°–140°.

Calcd: C, 61.07; H, 5.90; N, 5.28. Found: C, 61.00; H, 6.16; N, 5.33.

EXAMPLE 19

(±)-cis-2,3-Dihydro-3-methoxy-5-[2-(dimethylamino)ethyl]-2-(4-methoxyphenyl)naphtho[1,2-b]-1,4-thiazepin-4(5H)-one To a solution of 1.6 g of (±)-cis-2,3-dihydro-3-hydroxy-2-(4-methoxyphenyl)-5-[2-(dimethylamino)ethyl]naphtho[1,2-b]-1,4-thiazepin-4(5H)-one in 30 mL benzene, 0.21 g of sodium hydride (50% dispersion in mineral oil) was added and the mixture was heated at reflux for one hour. After cooling 0.6 g of dimethyl sulfate was added dropwise to the above mixture and stirred at room temperature for 17 hours. The reaction mixture was poured into ice-water and the aqueous suspension was extracted with ethyl acetate (3×75 mL). The combined solutions were washed with brine (50 mL), then dried (magnesium sulfate) and removal of the solvent at reduced pressure gave 0.9 g of a residue. The residue on crystallization from ether afforded 0.2 g of unreacted thiazepin starting material. The mother liquor after removal of thiazepin starting material was concentrated to dryness and the residue on treatment with hydrogen chloride (anhydrous) in acetone afforded the hydrochloride, which after recrystallization from acetone gave 0.35 g (23%) of (±)-cis-2,3-dihydro-3-methoxy-5-[2-(dimethylamino)ethyl]-2-(4-methoxyphenyl)naphtho[1,2-b]-1,4-thiazepin-4(5H)-one hydrochloride, mp 242°–243°.

Calcd: C, 63.48; H, 6.18; N, 5.92. Found: C, 63.29; H, 6.01; N, 5.89.

The above hydrochloride (0.35 g) in water was treated with concentrated ammonium hydroxide and the aqueous suspension was extracted with ether. The combined ether extracts were washed with brine and dried (magnesium sulfate). Removal of the solvent gave 0.25 g (78%) of (±)-cis-2,3-dihydro-3-methoxy-5-[2-(dimethylamino)ethyl]-2-(4-methoxyphenyl)naphtho[1,2-b]-1,4-thiazepin-4(5H)-one. A sample was crystallized from ether—pet. ether, mp 118°–120°.

Calcd: C, 68.79; H, 6.47; N, 6.42. Found: C, 68.89; H, 6.55; N, 6.32.

EXAMPLE 20

(±)-cis-2,3-Dihydro-3-[(4-(methoxyacetyl)oxy]-2-(4-methoxyphenyl)-5-[2-(dimethylamino)ethyl]naphtho[1,2-b]-1,4-thiazepin-4(5H)-one To a solution of 2.0 g of (±)-cis-2,3-dihydro-3-hydroxy-2-(4-methoxyphenyl)-5-[2-(dimethylamino)ethyl]naphtho[1,2-b]-1,4-thiazepin-4(5H)-one in 25 mL of pyridine (dried over potassium hydroxide) was added dropwise at ice-bath temperature, 0.9 g methoxyacetyl chloride and the mixture was kept at this temperature overnight. It was concentrated at reduced pressure and the residue was partitioned between ethyl acetate and dilute ammonium hydroxide. The combined ethyl acetate solutions were washed with brine and dried (magnesium sulfate). Removal of the solvent gave 2.3 g (48%) of (±)-cis-2,3-dihydro-3-[(4-methoxyacetyl)oxy]-2-(4-methoxyphenyl)-5-[2-(dimethylamino)ethyl]naphtho[1,2-b]-1,4-thiazepin-4(5H)-one as an amorphous compound.

Calcd: C, 65.57; H, 6.11; N, 5.66. Found: C, 65.56; H, 6.13; N, 5.56.

The above base (2.3 g) on treatment with hydrogen chloride (anhydrous) in acetone afforded the hydrochloride which after recrystallization from acetone gave 2.3 g of (±)-cis-2,3-dihydro-3-[(4-methoxyacetyl)oxy]-2-(4-methoxyphenyl)-5-[2-(dimethylamino)ethyl]naphtho[1,2-b]-1,4-thiazepin-4(5H)-one hydrochloride, mp 241°–242°.

Calcd: C, 61.06; H, 5.88; N, 5.27. Found: C, 60.88; H, 5.92; N, 5.24.

EXAMPLE 21

(±)-cis-3-[(Cyclopropylcarbonyl)oxy]-2,3-dihydro-5-[2-(dimethylamino)ethyl]-2-(4-methoxyphenyl)naphtho[1,2-b]-1,4-thiazepin-4(5H)-one To a solution of 2.0 g of (±)-cis-2,3-dihydro-3-hydroxy-2-(4-methoxyphenyl)-5-[2-(dimethylamino)ethyl]naphtho[1,2-b]-1,4-thiazepin-4(5H)-one in 25 mL pyridine was added dropwise at ice-bath temperature 0.9 g of cyclopropanecarboxylic acid chloride and the solution was kept at this temperature for 17 hours. The mixture was concentrated and the residue, in water, was made basic with concentrated ammonium hydroxide. The aqueous suspension was extracted with ethyl acetate (3×60 mL). The combined ethyl acetate solutions were washed with brine and dried (magnesium sulfate). Removal of the solvent gave 2.3 g (100%) of (±)-cis-3-[(cyclopropylcarbonyl)oxy]-2,3-dihydro-5-[2-(dimethylamino)ethyl]-2-(4-methoxyphenyl)naphtho[1,2-b]-1,4-thiazepin-4(5H)-one as an amorphous compound.

Calcd: C, 68.55; H, 6.16; N 5.71. Found: C, 68.31; H, 6.22; N, 5.63.

The above base (2.3 g) on treatment with hydrogen chloride (anhydrous) in acetone afforded 1.7 g (85%) of (±)-cis-3-[(cyclopropylcarbonyl)oxy]-2,3-dihydro-5-[2-

(dimethylamino)ethyl]-2-(4-methoxyphenyl)naphtho[1,2-b]-1,4-thiazepin-4(5H)-one hydrochloride, mp 186°–187°.

Calcd: C, 63.91; H, 5.93; N, 5.31. Found: C, 64.01;; H, 6.14; N, 5.58.

EXAMPLE 22

(±)-cis-5-[2-(Diethylamino)ethyl]-2,3-dihydro-3-hydroxy-2-(4-methoxyphenyl)naphtho[1,2-b]-1,4-thiazepin-4(5H)-one A mixture of 4.4 g of (±)-cis-2,3-dihydro-3-hydroxy-2-(4-methoxyphenyl)naphtho[1,2-b]-1,4-thiazepin-4(5H)-one, 2.0 g of potassium carbonate and 1.8 g of 2-diethylaminoethyl chloride in 100 mL ethyl acetate was stirred and heated at reflux for 2 hours then an additional 0.5 g of 2-diethylaminoethyl chloride was added four times at 2 hour intervals. The mixture was heated at reflux for a total of 12 hours, then cooled to room temperature and to the mixture ethyl acetate and water were added. The organic phase was separated, washed with brine and dried (magnesium sulfate). Removal of the solvent gave the product which after crystallization from ether afforded 4.9 g (87%) (±)-cis-5-[2-(diethylamino)ethyl]-2,3-dihydro-3-hydroxy-2-(4-methoxyphenyl)naphtho[1,2-b]-1,4-thiazepin-4(5H)-one, mp 124°–125°.

Calcd: C, 69.31; H, 6.71; N, 6.22. Found: C, 69.35; H, 6.58; N, 6.16.

The above base (4.9 g) on treatment with hydrogen chloride (anhydrous) in acetone afforded 4.5 g (86%) of (±)-cis-5-[2-(diethylamino)ethyl]-2,3-dihydro-3-hydroxy-2-(4-methoxyphenyl)naphtho[1,2-b]-1,4-thiazepin-4(5H)-one hydrochloride, mp 211°–212°.

Calcd: C, 64.12; H, 6.42; N, 5.75. Found: C, 63.91; H, 6.49; N, 5.52.

EXAMPLE 23

(±)-cis-3-(Acetyloxy)-5-[2-(diethylamino)ethyl]-2,3-dihydro-2-(4-methoxyphenyl)naphtho[1,2-b]-1,4-thiazepin-4(5H)-one A mixture of 2.5 g of (±)-cis-2,3-dihydro-3-hydroxy-2-(4-methoxyphenyl)-5-[2-(diethylamino)ethyl]naphtho[1,2-b]-1,4-thiazepin-4(5H)-one hydrochloride and 25 mL of acetic anhydride was stirred and heated at 100° for 17 hours. The excess of reagent was removed under reduced pressure and the residue was crystallized from ethyl acetate to give 2.5 g (93%) of (±)-cis-3-(acetyloxy)-5-[2-(diethylamino)ethyl]-2,3-dihydro-2-(4-methoxyphenyl)naphtho[1,2-b]-1,4-thiazepin-4(5H)-one hydrochloride, mp 211°–212°.

Calcd: C, 63.56; H, 6.29; N, 5.29. Found: C, 63.32; H, 6.41; N, 5.30.

A sample of the above hydrochloride, in water was treated with concentrated ammonium hydroxide and the aqueous suspension was extracted with ether. The ether solutions were washed with water and dried (magnesium sulfate). Removal of the solvent gave the base, which after crystallization from ether afforded (±)-cis-3-(acetyloxy)-5-[2-(diethylamino)ethyl]-2,3-dihydro-2-(4-methoxyphenyl)naphtho[1,2-b]-1,4-thiazepin-4(5H)-one, mp 148°–149°.

Calcd: C, 68.27; H, 6.55; N, 5.69. Found: C, 68.43; H, 6.59; N, 5.68.

EXAMPLE 24

(±)-cis-2,3-Dihydro-3-hydroxy-5-[3-(dimethylamino)propyl]-2-(4-methoxyphenyl)naphtho[1,2-b]-1,4-thiazepin-4(5H)-one A mixture of 1.7 g of (±)-cis-2,3-dihydro-3-hydroxy-2-(4-methoxyphenyl)naphtho[1,2-b]-1,4-thiazepin-4(5H)-one, 0.75 g potassium carbonate and 0.7 g of 3-dimethylaminopropyl chloride in 30 mL of ethyl acetate was stirred and heated at reflux for 2 hours then an additional 0.2 g of 3-dimethylaminopropyl chloride was added four times at 2 hour intervals. The mixture was heated at reflux for a total of 12 hours then to the mixture ethyl acetate and water were added. The organic phase was separated, washed with brine and dried (magnesium sulfate). Removal of the solvent gave 2.1 g (100%) (±)-cis-2,3-dihydro-3-hydroxy-5-[3-(dimethylamino)propyl]-2-(4-methoxyphenyl)naphtho[1,2-b]-1,4-thiazepin-4(5H)-one. A sample was crystallized from ether, mp 123°–124°.

Calcd: C, 68.78; H, 6.46; N, 6.42. Found: C, 68.92; H, 6.44; N, 6.43.

The above base (2.1 g) on treatment with hydrogen chloride (anhydrous) in acetone afforded 1.3 g (59%) of (±)-cis-2,3-dihydro-3-hydroxy-5-[3-(dimethylamino)propyl]-2-(4-methoxyphenyl)naphtho[1,2-b]-1,4-thiazepin-4(5H)-one hydrochloride. A sample was recrystallized from acetonitrile, mp 234°–235°.

Calcd: C, 63.48; H, 6.18; N, 5.92. Found: C, 63.68; H, 6.30; N, 6.30.

EXAMPLE 25

(±)-cis-3-(Acetyloxy)-2,3-dihydro-5-[3-(dimethylamino)propyl]-2-(4-methoxyphenyl)naphtho[1,2-b]-1,4-thiazepin-4(5H)-one A mixture of 2.6 g of (±)-cis-2,3-dihydro-3-hydroxy-5-[3-(dimethylamino)propyl]-2-(4-methoxyphenyl)-naphtho[1,2-b]-1,4-thiazepin-4(5H)-one hydrochloride and 25 mL of acetic anhydride was stirred and heated at 100° for 17 hours. The excess of reagent was removed under reduced pressure and the residue was dissolved in water. The aqueous solution was made basic with concentrated ammonium hydroxide and extracted with ethyl acetate (3×75 mL). The combined ethyl acetate solutions were washed with brine (50 mL) and dried (magnesium sulfate). Removal of the solvent gave 2.2 g (84%) (±)-cis-3-(acetyloxy)-2,3-dihydro-5-[3-(dimethylamino)propyl]-2-(4-methoxyphenyl)naphtho[1,2-b]-1,4-thiazepin-4(5H)-one. A sample of this compound was crystallized from ether, mp 98°–99°.

Calcd: C, 67.76; H, 6.32; N, 5.85. Found: C, 67.58; H, 6.58; N, 5.68.

The above base (2.2 g) on treatment with hydrogen chloride (anhydrous) in acetone afforded the hydrochloride which after recrystallization from acetone gave 1.2 g (52%) of (±)-cis-3-(acetyloxy)-2,3-dihydro-5-[3-(dimethylamino)propyl]-2-(4-methoxyphenyl)-naphtho[1,2-b]-1,4-thiazepin-4(5H)-one hydrochloride, mp 135°–137°.

Calcd: C, 62.96; H, 6.07; N, 5.44. Found: C, 62.76; H, 6.26; N, 5.50.

EXAMPLE 26

(±)-cis-2,3-dihydro-3-hydroxy-2-(4-methoxyphenyl)-naphtho-5-[2-[methyl(phenylmethyl)amino]ethyl]-[1,2-b]-1,4-thiazepin-4(5H)-one A mixture of 2.8 g of ±-cis-2,3-dihydro-3-hydroxy-2-(4-methoxyphenyl)naphtho[1,2-b]-1,4-thiazepin-4(5H)-one, 1.0 g of powdered potassium carbonate, 1.3 g of powdered potassium iodide and 1.5 g of β-(N-benzyl-N-methyl-amino)ethyl chloride in 75 ml ethyl acetate was stirred and heated at reflux for two hours, then an additional 1.5 g of β-(N-benzyl-N-methylamino)ethyl chloride in 0.5 g portions was added at 2, 3 and 10 hour intervals. The mixture was heated at reflux for a total of 17 hours, then was cooled to room temperature and diluted with water. The aqueous suspension was extracted with ethyl acetate (2×150 ml). The combined ethyl acetate solutions were dried (magnesium sulfate), filtered and removal of the solvent gave 5.9 g of product which was chromatographed on a column using 80 g of silica gel. The column was eluted with 30 ml portions of ethyl acetate. Fractions 5 through 9 were combined and the solvent was removed under reduced pressure to give 1.25 g (32%) of (±)-cis-2,3-dihydro-3-hydroxy-2-(4-methoxyphenyl)naphtho-5-[2-[methyl(phenylmethyl)amino]ethyl]-[1,2-b]-1,4-thiazepin-4(5H)-one as an amorphous compound.

Calcd: C, 72.27; H, 6.07; N, 5.62. Found: C, 72.33; H, 6.32; N, 5.65.

EXAMPLE 27

(±)-cis-3-(Acetyloxy)-2,3-dihydro-2-(4-methoxyphenyl)naphtho-5-[2-[methyl(phenylmethyl)]amino]ethyl]-[1,2-b]-1,4-thiazepin-4(5H)-one To a solution of 1.5 g of (±)-cis-2,3-dihydro-3-hydroxy-2-(4-methoxyphenyl)naphtho-5-[2-[methyl(phenylmethyl)amino]ethyl]-[1,2-b]-1,4-thiazepin-4(5H)-one in 25 mL of pyridine was added dropwise at ice-bath temperature 0.5 g of acetyl chloride and the solution was kept at this temperature for 2 hours. The mixture was concentrated and the residue in water was made basic with concentrated ammonium hydroxide. The aqueous suspension was extracted with ethyl acetate. The combined ethyl acetate solutions were washed with brine and dried. Removal of the solvent gave 1.5 g (92%) of crude (±)-cis-3-(acetyloxy)-2,3-dihydro-2-(4-methoxyphenyl)naphtho-5-[2-[methyl(phenylmethyl)-]amino]ethyl]-[1,2-b]-1,4-thiazepin-4(5H)-one as an amorphous compound. This base (1.5 g) on treatment with hydrogen chloride (anhydrous) in acetone afforded 1.1 g (69%) of (±)-cis-3-(acetyloxy)-2,3-dihydro-2-(4-methoxyphenyl)naphtho-5-[2-[methyl(phenylmethyl)]amino]ethyl[1,2-b]-1,4-thiazepin-4(5H)-one hydrochloride, mp. 228°–229°.

Calcd: C, 66.71; H, 5.78; N, 4.86. Found: C, 66.30; H, 5.71 N, 4.83.

EXAMPLE 28

| | Tablets | | |
|---|---|---|---|
| | | mg/tablet | |
| Item | Ingredient | 100 mg | 200 mg |
| 1. | (+)-cis-3-(Acetyloxy)-2,3-dihydro-2-(4-methoxyphenyl)-5-[2-(dimethylamino)ethyl] naphtho[1,2-b]-1,4-thiazepin-4(5H)—one hydrochloride | 100 | 200 |
| 2. | Lactose | 100 | 200 |
| 3. | Polyvinylpyrrolidone (PVP) | 10 | 20 |
| 4. | Modified Starch | 10 | 20 |
| 5. | Magnesium Stearate | 3 | 6 |
| | | 223 mg | 446 mg |

(1) Mix Items 1, 2 and 4 and granulate with PVP in water or alcohol.
(2) Dry the granulation at 45° C.
(3) Mill the dried granulation through a suitable mill.
(4) Add Item 5 and mix for three minutes and compress on a suitable press.

EXAMPLE 29

| | Capsules | | |
|---|---|---|---|
| | | mg/tablet | |
| Item | Ingredient | 100 mg | 200 mg |
| 1. | (+)-cis-3-(Acetyloxy)-2,3-dihydro-2-(4-methoxyphenyl)-5-[2-(dimethylamino)ethyl] naphtho[1,2-b]-1,4-thiazepin-4(5H)—one hydrochloride | 100 | 200 |
| 2. | Corn Starch (Pregelatinized) | 50 | 80 |
| 3. | Modified Starch | 10 | 20 |
| 4. | Talc | 20 | 20 |
| 5. | Magnesium Stearate | 1 | 1 |
| | | 181 mg | 322 mg |

(1) Mix Items 1–3 and wet granulate with water. Dry at 45° C. overnight.
(2) Mill through suitable screen using appropriate milling equipment.
(3) Add Items 4 and 5 and mix for five minutes.
(4) Fill into suitable capsule.

EXAMPLE 30

| | Parenteral Solution | |
|---|---|---|
| Item | Ingredient | mg/ml |
| 1. | (±)-cis-3-(Acetyloxy)-2,3-dihydro-2-(4-methoxyphenyl)-5-[2-(dimethylamino)ethyl] naphtho[1,2-b]-1,4-thiazepin-4(5H)—one hydrochloride | 10 |
| 2. | Benzyl Alcohol | 10 |
| 3. | Sorbitol | 38 |
| 4. | Hydrochloric Acid q.s. to pH | 3–7 |
| 5. | Sodium Hydroxide q.s. to pH | 3–7 |
| 6. | Water for Injection q.s. to | 1 ml |

In the above parenteral solution q.s. means sufficient quantity.

We claim:

1. A compound of the formula:

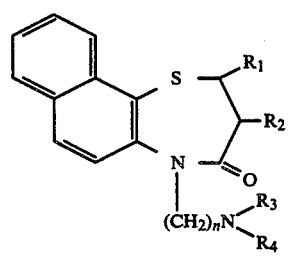

wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy,

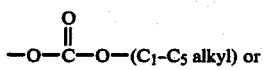

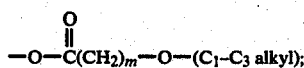

$R_3$ and $R_4$ are independently lower alkyl, phenyl lower alkyl, or together form a pyrrolidine or piperidine ring; n is 2 to 4; m is 1 to 2; or a pharmaceutically acceptable acid addition salt thereof.

2. A compound in accordance with claim 1, of the formula

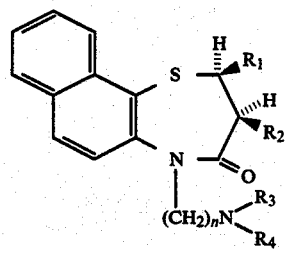

I' wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy,

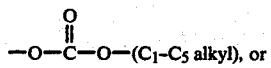

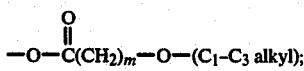

$R_3$ and $R_4$ are independently lower alkyl, phenyl lower alkyl or together form a piperidine or pyrrolidine ring; n is 2 to 4; m is 1 to 2; an enantiomer or a racemate thereof or a pharmaceutically acceptable acid addition salt thereof.

3. A compound in accordance with claim 2, of the formula

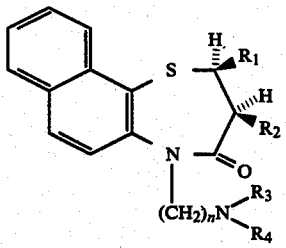

I' wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy,

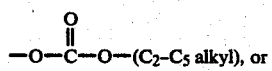

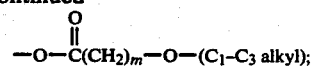

$R_3$ and $R_4$ are independently lower alkyl, phenyl lower alkyl or together form a piperidine or pyrrolidine ring; n is 2 to 4; m is 1 to 2; or a pharmaceutically acceptable acid addition salt thereof.

4. A compound in accordance with claim 2, wherein $R_1$ is 4-lower alkoxyphenyl and $R_2$ is hydroxy.

5. A compound in accordance with claim 4, wherein $R_1$ is 4-methoxyphenyl, $R_3$ and $R_4$ are independently lower alkyl and n is 2 to 3.

6. A compound in accordance with claim 5 (−)-cis-2,3-dihydro-3-hydroxy-2-(4-methoxyphenyl)-5-[2-(dimethylamino)ethyl]naphtho[1,2-b]-1,4-thiazepin-4(5H)-one, or the hydrochloride salt thereof.

7. A compound in accordance with claim 5, (±)-cis-5-[2-(dimethylamino)ethyl]-2,3-dihydro-3-hydroxy-2-(4-methoxyphenyl)naphtho[1,2-b]-1,4-thiazepin-4(5H)-one, or the hydrochloride salt thereof.

8. A compound in accordance with claim 3, wherein $R_1$ is 4-lower alkoxyphenyl and $R_2$ is hydroxy.

9. A compound in accordance with claim 8, wherein $R_1$ is 4-methoxyphenyl, $R_3$ and $R_4$ are independently lower alkyl, and n is 2 to 3.

10. A compound in accordance with claim 9, (+)-cis-5-[2-(dimethylamino)ethyl]-2,3-dihydro-3-hydroxy-2-(4-methoxyphenyl)naphtho[1,2-b]-1,4-thiazepin-4(5H)-one, or the hydrochloride salt thereof.

11. A compound in accordance with claim 2, wherein $R_1$ is 4-lower alkoxyphenyl and $R_2$ is selected from the group consisting of acetyloxy and propionyloxy.

12. A compound in accordance with claim 11, wherein $R_1$ is 4-methoxyphenyl, $R_2$ is acetyloxy, $R_3$ and $R_4$ are independently lower alkyl, and n is 2 to 3.

13. A compound in accordance with claim 12, (±)-cis-3-(acetyloxy)-5-[2-(dimethylamino)ethyl]-2,3-dihydro-2-(4-methoxyphenyl)naphtho[1,2-b]-1,4-thiazepin-4(5H)-one, or the hydrochloride salt thereof.

14. A compound in accordance with claim 12, (−)-cis-3-(acetyloxy)-2,3-dihydro-2-(4-methoxyphenyl)-5-[2-(dimethylamino)ethyl]naphtho[1,2-b]-1,4-thiazepin-4(5H)-one, or the hydrochloride salt thereof.

15. A compound in accordance with claim 1 of the formula

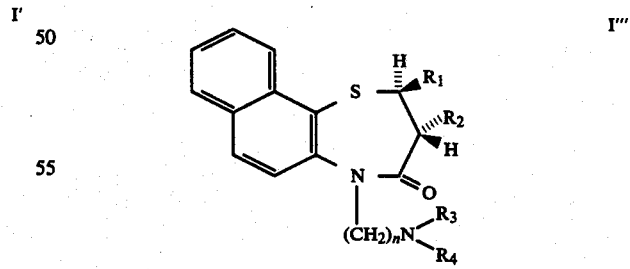

I''' wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy, -continued

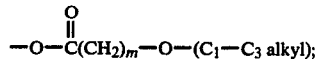

$R_3$ and $R_4$ are independently lower alkyl, phenyl lower alkyl or together form a piperidine or pyrrolidine ring; n is 2 to 4; m is 1 to 2; an enantiomer or a racemate thereof or a pharmaceutically acceptable acid addition salt thereof.

16. A compound in accordance with claim 15, (±)-trans-3-(acetyloxy)-2,3-dihydro-2-(4-methoxyphenyl)-5-[2-(dimethylamino)ethyl]naphtho[1,2-b]-1,4-thiazepin-4(5H)-one, or the hydrochloride salt thereof.

17. A compound in accordance with claim 3, wherein $R_1$ is 4-lower alkoxyphenyl and $R_2$ is selected from the group consisting of acetyloxy and propionyloxy.

18. A compound in accordance with claim 17, wherein $R_1$ is 4-methoxyphenyl, $R_2$ is acetyloxy, $R_3$ and $R_4$ are independently lower alkyl and n is 2 to 3.

19. A compound in accordance with claim 18, (+)-cis-3-(acetyloxy)-2,3-dihydro-2-(4-methoxyphenyl)-5-[2-(dimethylamino)ethyl]naphtho[1,2-b]-1,4-thiazepin-4(5H)-one, or the hydrochloride salt thereof.

20. A compound in accordance with claim 2, wherein $R_1$ is 4-lower alkoxyphenyl and $R_2$ is

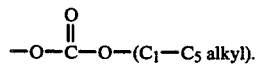

21. A compound in accordance with claim 20, (±)-cis-3-[(ethoxycarbonyl)oxy]-2,3-dihydro-2-(4-methoxyphenyl)-5-[2-(dimethylamino)ethyl]naphtho[1,2-b]-1,4-thiazepin-4(5H)-one, or the hydrochloride salt thereof.

22. A compound in accordance with claim 2, wherein $R_1$ is 4-lower alkoxyphenyl and $R_2$ is lower alkoxy.

23. A compound in accordance with claim 22, (±)-cis-2,3-dihydro-3-methoxy-5-[2-(dimethylamino)ethyl]-2-(4-methoxyphenyl)naphtho[1,2-b]-1,4-thiazepin-4(5H)-one, or the hydrochloride salt thereof.

24. A compound in accordance with claim 23, wherein $R_1$ is 4-lower alkoxyphenyl and $R_2$ is

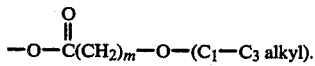

25. A compound in accordance with claim 24, (±)-cis-2,3-dihydro-3-[4-(methoxyacetyl)oxy]-2-(4-methoxyphenyl)-5-[2-(dimethylamino)ethyl]naphtho[1,2-b]-1,4-thiazepin-4(5H)-one, or the hydrochloride salt thereof.

26. A compound in accordance with claim 2, wherein $R_1$ is 4-methoxyphenyl and $R_2$ is lower cycloalkylcarbonyloxy.

27. A compound in accordance with claim 26, (±)-cis-3-[(cyclopropylcarbonyl)oxy]-2,3-dihydro-5-[2-(dimethylamino)ethyl]-2-(4-methoxyphenyl)naphtho[1,2-b]-1,4-thiazepin-4(5H)-one, or the hydrochloride salt thereof.

28. A compound of the formula

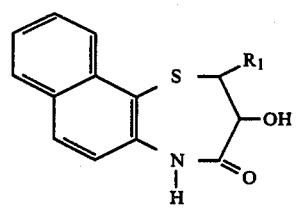

VI wherein $R_1$ is phenyl substituted with 1 to 3 lower alkoxy groups or 1 to 3 halogens.

29. A compound in accordance with claim 28, of the formula

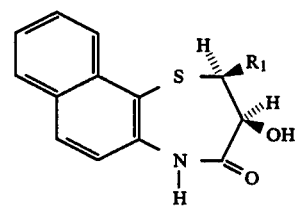

VI' wherein $R_1$ is phenyl substituted with 1 to 3 lower alkoxy groups or 1 to 3 halogens; an enantiomer or a racemate thereof.

30. A compound in accordance with claim 29, wherein $R_1$ is 4-lower alkoxy phenyl.

31. A compound in accordance with claim 30, (±)-cis-2,3-dihydro-3-hydroxy-2-(4-methoxyphenyl)-naphtho[1,2-b]-1,4-thiazepin-4(5H)-one.

32. A compound in accordance with claim 2, wherein $R_1$ is 4-lower alkoxyphenyl, $R_2$ is hydroxy or lower alkanoyloxy, $R_3$ is phenyl lower alkyl, $R_4$ is lower alkyl and n is 2 to 3.

33. A compound in accordance with claim 32, (±)-cis-3-(acetyloxy)-2,3-dihydro-2-(4-methoxyphenyl)-5-[2-[methyl(phenylmethyl)ethyl]amino]naphtho[1,2-b]-1,4-thiazepin-4(5H)-one, or the hydrochloride salt thereof.

34. A composition with calcium antagonist activity comprising an effective amount of a compound of the formula

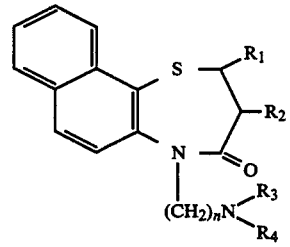

I wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy,

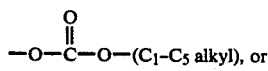

-continued

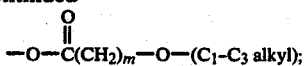

R₃ and R₄ are independently lower alkyl or together form a piperidine or pyrrolidine ring; n is 2 to 4; m is 1 to 2; or a pharmaceutically acceptable acid addition salt thereof, and a pharmaceutically inert carrier material.

35. A composition in accordance with claim 34, comprising a compound of the formula

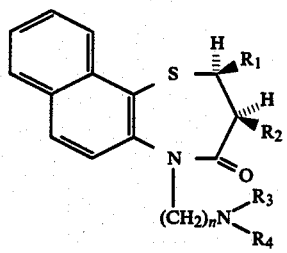

I' wherein R₁ is phenyl substituted with 1 to 3 lower alkoxy groups or 1 to 3 halogens; R₂ is hydroxy, lower alkoxy, lower alkanoyloxy, lower cycloalkylcarbonyloxy,

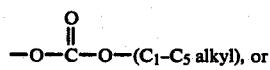

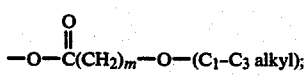

R₃ and R₄ are independently lower alkyl, phenyl lower alkyl or together form a piperidine or pyrrolidine ring; n is 2 to 4; m is 1 to 2; an enantiomer or a racemate thereof, or a pharmaceutically acceptable acid addition salt thereof.

36. A composition in accordance with claim 35, of the formula

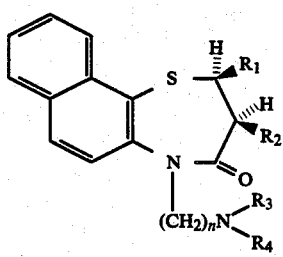

I' wherein R₁ is phenyl substituted with 1 to 3 lower alkoxy groups or 1 to 3 halogens; R₂ is hydroxy, lower alkoxy, lower alkanoyloxy, lower cycloalkylcarbonyloxy,

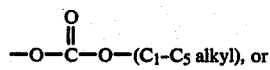

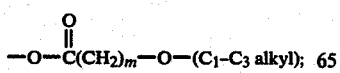

R₃ and R₄ are independently lower alkyl, phenyl lower alkyl or together form a piperidine or pyrrolidine ring; n is 2 to 4; m is 1 to 2; or a pharmaceutically acceptable acid addition salt thereof.

37. A composition in accordance with claim 36, wherein R₁ is 4-lower alkoxyphenyl and R₂ is selected from the group consisting of acetyloxy and propionyloxy.

38. A composition in accordance with claim 37, wherein the compound of formula I' is: (+)-cis-3-(acetyloxy)-2,3-dihydro-2-(4-methoxyphenyl)-5-[2-(dimethylamino)ethyl]naphtho[1,2-b]-1,4-thiazepin-4(5H)-one, or the hydrochloride salt thereof.

39. A method of inducing calcium antagonist activity which comprises administering to a warm-blooded animal in need of such treatment, an effective amount of a compound of the formula

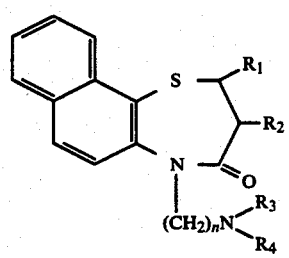

I wherein R₁ is phenyl substituted with 1 to 3 lower alkoxy groups or 1 to 3 halogens; R₂ is hydroxy, lower alkoxy, lower alkanoyloxy, lower cycloalkylcarbonyloxy,

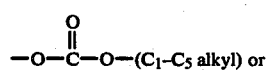

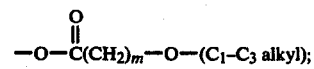

R₃ and R₄ are independently lower alkyl, phenyl lower alkyl or together form a piperidine or pyrrolidine ring; n is 2 to 4; m is 1 to 2, or a pharmaceutically acceptable acid addition thereof.

40. A method in accordance with claim 39 which comprises administering a compound of the formula

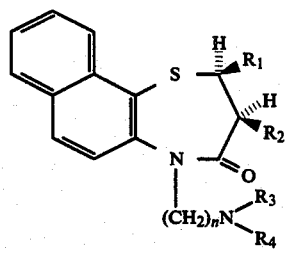

I' wherein R₁ is phenyl substituted with 1 to 3 lower alkoxy groups or 1 to 3 halogens; R₂ is hydroxy, lower alkoxy, lower alkanoyloxy, lower cycloalkylcarbonyloxy,

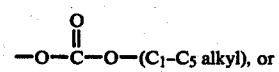

-continued

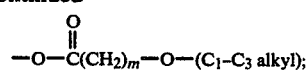

$R_3$ and $R_4$ are independently lower alkyl, phenyl lower alkyl or together form a piperidine or pyrrolidine ring; n is 2 to 4; m is 1 to 2 or a racemate thereof, or a pharmaceutically acceptable acid addition salt thereof.

41. A method in accordance with claim 40, which comprises administering a compound of the formula

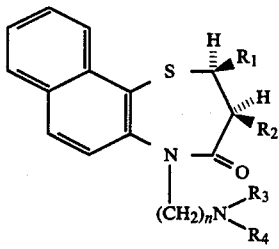

I' wherein $R_1$ is phenyl substituted with 1 to 3 lower alkoxy groups or 1 to 3 halogens; $R_2$ is hydroxy, lower alkoxy, lower alkanoyloxy, lower cycloalkylcarbonyloxy,

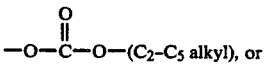

or

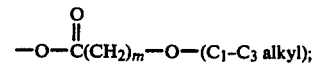

$R_3$ and $R_4$ are independently lower alkyl, phenyl lower alkyl or together form a piperidine or pyrrolidine ring; n is 2 to 4; m is 1 to 2; or a pharmaceutically acceptable acid addition salt thereof.

42. A method in accordance with claim 41, wherein $R_1$ is 4-lower alkoxyphenyl and $R_2$ is selected from the group consisting of acetyloxy and propionyloxy.

43. A method in accordance with claim 42, wherein the compound of formula I' is: (+)-cis-3-(acetyloxy)-2,3-dihydro-2-(4-methoxyphenyl)-5-[2-(dimethylamino)ethyl]naphtho[1,2-b]-1,4-thiazepin-4(5H)-one, or the hydrochloride salt thereof.

* * * * *